US011581097B2

(12) United States Patent
Chaudhri et al.

(10) Patent No.: US 11,581,097 B2
(45) Date of Patent: Feb. 14, 2023

(54) SYSTEMS AND METHODS FOR PATIENT RETENTION IN NETWORK THROUGH REFERRAL ANALYTICS

(71) Applicant: Apixio, Inc., San Mateo, CA (US)

(72) Inventors: Imran N. Chaudhri, Potomac, MD (US); Shahram Shawn Dastmalchi, San Ramon, CA (US); Robert Derward Rogers, Oakland, CA (US); Vishnuvyas Sethumadhavan, Mountain View, CA (US); Shamshad Alam Ansari, San Mateo, CA (US)

(73) Assignee: APIXIO, INC., San Mateo, CA (US)

( * ) Notice: Subject to any disclaimer, the term of this patent is extended or adjusted under 35 U.S.C. 154(b) by 0 days.

(21) Appl. No.: 16/775,177

(22) Filed: Jan. 28, 2020

(65) Prior Publication Data

US 2020/0234315 A1 Jul. 23, 2020

Related U.S. Application Data

(63) Continuation of application No. 13/798,031, filed on Mar. 12, 2013, now abandoned, which is a (Continued)

(51) Int. Cl.
*G16H 70/20* (2018.01)
*G16H 10/60* (2018.01)
(Continued)

(52) U.S. Cl.
CPC ......... *G16H 70/20* (2018.01); *G06Q 30/0201* (2013.01); *G16H 10/60* (2018.01); *G16H 50/20* (2018.01)

(58) Field of Classification Search
CPC ..................................................... G16H 70/20
See application file for complete search history.

(56) References Cited

U.S. PATENT DOCUMENTS

| 5,164,899 A | 11/1992 | Sobotka et al. |
| 5,307,262 A | 4/1994 | Ertel |

(Continued)

FOREIGN PATENT DOCUMENTS

| JP | 09135816 A | 5/1997 |
| JP | H1145304 A | 2/1999 |

(Continued)

OTHER PUBLICATIONS

Lemeshow et al, Searching one or two databases was insufficient for meta-analysis of observational studies, 7 pages (Year: 2005).

(Continued)

*Primary Examiner* — Robert A Sorey
*Assistant Examiner* — Kristine K Rapillo
(74) *Attorney, Agent, or Firm* — Armstrong Teasdale LLP

(57) ABSTRACT

A medical information navigation engine ("MINE") is capable of inferring referral activity not reported into a referral workflow system by utilizing intent-based clustering of medical information. The intent based clustering reconciles received medical data, from a variety of sources, and then clusters the data by applying one or more clustering rules. After the referrals not otherwise reported are inferred, they may be utilized to generate metrics that can be utilized to enhance patient care, and reduce costs. Metrics may be generated for both in-network and out-of-network referrals in order to distinguish differences in reporting activity.

15 Claims, 18 Drawing Sheets

Related U.S. Application Data continuation-in-part of application No. 13/223,228, filed on Aug. 31, 2011, now Pat. No. 10,176,541.

(60) Provisional application No. 61/754,527, filed on Jan. 18, 2013, provisional application No. 61/379,228, filed on Sep. 1, 2010.

(51) Int. Cl.

| | | |
|---|---|---|
| *G16H 50/20* | (2018.01) | |
| *G06Q 30/02* | (2012.01) | |
| *G06Q 30/0201* | (2023.01) | |

(56) References Cited

U.S. PATENT DOCUMENTS

| | | |
|---|---|---|
| 5,544,044 A | 8/1996 | Leatherman |
| 5,875,263 A | 2/1999 | Froessl |
| 6,076,088 A | 6/2000 | Paik |
| 6,209,095 B1 | 3/2001 | Anderson |
| 6,266,645 B1 | 7/2001 | Simpson |
| 6,336,108 B1 | 1/2002 | Thiesson et al. |
| 6,341,265 B1 | 1/2002 | Provost et al. |
| 6,505,196 B2 | 1/2003 | Drucker et al. |
| 6,601,055 B1 | 7/2003 | Roberts |
| 6,874,085 B1 | 3/2005 | Koo et al. |
| 7,321,861 B1 | 1/2008 | Oon |
| 7,702,524 B1 | 4/2010 | Whibbs et al. |
| 7,925,678 B2 | 4/2011 | Botros et al. |
| 8,254,681 B1 | 8/2012 | Poncin et al. |
| 8,380,530 B2 | 2/2013 | Marshall |
| 8,620,078 B1 | 12/2013 | Chapleau et al. |
| 8,977,076 B2 | 3/2015 | Samadani et al. |
| 9,495,515 B1 | 11/2016 | Kennedy et al. |
| 10,628,553 B1 | 4/2020 | Murrish et al. |
| 2001/0042080 A1 | 11/2001 | Ross |
| 2002/0007284 A1 | 1/2002 | Schurenberg et al. |
| 2002/0010679 A1 | 1/2002 | Felsher |
| 2002/0103834 A1 | 8/2002 | Thompson et al. |
| 2002/0120466 A1 | 8/2002 | Finn |
| 2002/0143562 A1 | 10/2002 | Lawrence |
| 2002/0188182 A1 | 12/2002 | Haines et al. |
| 2003/0004748 A1 | 1/2003 | Coleman et al. |
| 2003/0046280 A1 | 3/2003 | Rotter et al. |
| 2003/0084043 A1 | 5/2003 | Acharya et al. |
| 2003/0120458 A1 | 6/2003 | Rao et al. |
| 2003/0120640 A1 | 6/2003 | Ohta et al. |
| 2003/0220915 A1 | 11/2003 | Fagan et al. |
| 2003/0229510 A1 | 12/2003 | Kerr |
| 2004/0073458 A1 | 4/2004 | Jensen |
| 2004/0076264 A1 | 4/2004 | Sorenson |
| 2004/0109028 A1 | 6/2004 | Stern et al. |
| 2004/0122702 A1 | 6/2004 | Sabol et al. |
| 2004/0172297 A1 | 9/2004 | Rao et al. |
| 2004/0220895 A1 | 11/2004 | Carus et al. |
| 2004/0249667 A1 | 12/2004 | Oon |
| 2005/0043986 A1 | 2/2005 | McConnell et al. |
| 2005/0251422 A1 | 5/2005 | Wolfman |
| 2005/0137912 A1 | 6/2005 | Rao et al. |
| 2005/0138017 A1 | 6/2005 | Keen et al. |
| 2005/0154690 A1 | 7/2005 | Nitta et al. |
| 2005/0182659 A1 | 8/2005 | Huttin |
| 2005/0192792 A1 | 9/2005 | Carus et al. |
| 2005/0203773 A1 | 9/2005 | Soto et al. |
| 2005/0228593 A1 | 10/2005 | Jones |
| 2005/0240439 A1 | 10/2005 | Covit et al. |
| 2005/0283062 A1 | 12/2005 | Hoffman et al. |
| 2006/0026036 A1 | 2/2006 | Mahmood |
| 2006/0026525 A1 | 2/2006 | Fischer et al. |
| 2006/0036619 A1 | 2/2006 | Fuerst et al. |
| 2006/0047669 A1 | 3/2006 | Durrence et al. |
| 2006/0053098 A1 | 3/2006 | Gardner et al. |
| 2006/0112050 A1 | 5/2006 | Miikkulainen et al. |
| 2006/0129435 A1 | 6/2006 | Smitherman et al. |
| 2006/0179016 A1 | 8/2006 | Forman et al. |
| 2006/0184475 A1 | 8/2006 | Krishnan et al. |
| 2006/0241978 A1 | 10/2006 | Yoshii |
| 2006/0265251 A1 | 11/2006 | Patterson |
| 2006/0265253 A1* | 11/2006 | Rao ............... G16H 70/20 705/3 |
| 2007/0016450 A1 | 1/2007 | Bhora et al. |
| 2007/0055545 A1 | 3/2007 | Maughan et al. |
| 2007/0055552 A1 | 3/2007 | St. Clair et al. |
| 2007/0061348 A1 | 3/2007 | Holland et al. |
| 2007/0061393 A1 | 3/2007 | Moore |
| 2007/0078680 A1 | 4/2007 | Wennberg |
| 2007/0083390 A1 | 4/2007 | Gorup et al. |
| 2007/0088559 A1 | 4/2007 | Kim |
| 2007/0106754 A1 | 5/2007 | Moore |
| 2007/0118399 A1 | 5/2007 | Avinash et al. |
| 2007/0162308 A1 | 7/2007 | Peters |
| 2007/0168461 A1 | 7/2007 | Moore |
| 2007/0192143 A1 | 8/2007 | Krishnan et al. |
| 2007/0219829 A1 | 9/2007 | Kay |
| 2007/0226211 A1 | 9/2007 | Heinze et al. |
| 2008/0040151 A1 | 2/2008 | Moore |
| 2008/0052255 A1 | 2/2008 | Fan et al. |
| 2008/0077443 A1 | 3/2008 | Singer |
| 2008/0091633 A1 | 4/2008 | Rappaport et al. |
| 2008/0097936 A1 | 4/2008 | Schmidtler et al. |
| 2008/0103828 A1 | 5/2008 | Squilla et al. |
| 2008/0120296 A1 | 5/2008 | Kariathungal et al. |
| 2008/0147441 A1 | 6/2008 | Kil |
| 2008/0195570 A1 | 8/2008 | Msafadi et al. |
| 2008/0208630 A1 | 8/2008 | Fors et al. |
| 2008/0250025 A1 | 10/2008 | Abhyanker |
| 2008/0256181 A1 | 10/2008 | Morita et al. |
| 2008/0263048 A1 | 10/2008 | Wise |
| 2008/0270120 A1 | 10/2008 | Pestian et al. |
| 2008/0270340 A1 | 10/2008 | Abrams et al. |
| 2008/0287746 A1 | 11/2008 | Reisman |
| 2008/0288292 A1 | 11/2008 | Bi et al. |
| 2008/0320029 A1 | 12/2008 | Stivoric et al. |
| 2009/0024615 A1 | 1/2009 | Pedro et al. |
| 2009/0048877 A1 | 2/2009 | Binns et al. |
| 2009/0070103 A1 | 3/2009 | Beggelman et al. |
| 2009/0076839 A1 | 3/2009 | Abraham-Fuchs et al. |
| 2009/0099876 A1 | 4/2009 | Whitman |
| 2009/0110287 A1 | 4/2009 | Bates et al. |
| 2009/0112882 A1 | 4/2009 | Maresh et al. |
| 2009/0125246 A1 | 5/2009 | Ruiz |
| 2009/0136102 A1 | 5/2009 | Kimpe et al. |
| 2009/0138287 A1 | 5/2009 | Hermann, Jr. |
| 2009/0198517 A1 | 8/2009 | Ruben et al. |
| 2009/0216696 A1 | 8/2009 | Downs et al. |
| 2009/0220175 A1 | 9/2009 | Tzadok et al. |
| 2009/0228303 A1 | 9/2009 | Faulkner et al. |
| 2009/0228909 A1 | 9/2009 | Huang |
| 2009/0238625 A1 | 9/2009 | Ming et al. |
| 2009/0259487 A1 | 10/2009 | Rao et al. |
| 2009/0265189 A1 | 10/2009 | Bartholomew et al. |
| 2009/0271221 A1 | 10/2009 | Aridi et al. |
| 2009/0287504 A1 | 11/2009 | Benjamin et al. |
| 2009/0326981 A1 | 12/2009 | Karkanias et al. |
| 2010/0036680 A1 | 2/2010 | Familant |
| 2010/0088107 A1 | 4/2010 | Ur et al. |
| 2010/0117799 A1 | 5/2010 | Dormer et al. |
| 2010/0131299 A1 | 5/2010 | Hasan et al. |
| 2010/0131438 A1 | 5/2010 | Pandya et al. |
| 2010/0131482 A1 | 5/2010 | Linthicum et al. |
| 2010/0145723 A1 | 6/2010 | Hudson et al. |
| 2010/0169123 A1 | 7/2010 | Maus et al. |
| 2010/0174579 A1 | 7/2010 | Hughes |
| 2010/0179827 A1 | 7/2010 | McCallie, Jr. et al. |
| 2010/0185496 A1 | 7/2010 | Hahn et al. |
| 2010/0228721 A1 | 9/2010 | Mok et al. |
| 2010/0274584 A1 | 10/2010 | Kim |
| 2010/0281036 A1 | 11/2010 | Inoue et al. |
| 2010/0310172 A1 | 12/2010 | Natarajan et al. |
| 2010/0324927 A1 | 12/2010 | Tinsley |
| 2010/0324936 A1 | 12/2010 | Vishnubhatla et al. |
| 2011/0004588 A1 | 1/2011 | Leitersdorf et al. |
| 2011/0072002 A1 | 3/2011 | Kirkby et al. |

(56) References Cited

U.S. PATENT DOCUMENTS

| | | | |
|---|---|---|---|
| 2011/0077972 A1* | 3/2011 | Breitenstein | G16H 10/60 705/3 |
| 2011/0078145 A1 | 3/2011 | Chung et al. | |
| 2011/0093293 A1 | 4/2011 | G. N. et al. | |
| 2011/0093334 A1* | 4/2011 | Wood | G06Q 30/0255 705/14.53 |
| 2011/0117799 A1 | 5/2011 | Harada et al. | |
| 2011/0119089 A1 | 5/2011 | Carlisle | |
| 2011/0131062 A1 | 6/2011 | Menschik et al. | |
| 2011/0196702 A1 | 8/2011 | Salouk et al. | |
| 2011/0225001 A1 | 9/2011 | Shen | |
| 2011/0251989 A1 | 10/2011 | Kraaij et al. | |
| 2011/0258001 A1 | 10/2011 | Green et al. | |
| 2011/0264665 A1 | 10/2011 | Mital et al. | |
| 2011/0270632 A1 | 11/2011 | Manning et al. | |
| 2011/0295775 A1 | 12/2011 | Wang et al. | |
| 2012/0041772 A1 | 2/2012 | Ebadollahi et al. | |
| 2012/0060216 A1 | 3/2012 | Chaudhri et al. | |
| 2012/0066017 A1 | 3/2012 | Siegel | |
| 2012/0089412 A1 | 4/2012 | Bardy et al. | |
| 2012/0089606 A1 | 4/2012 | Eshwar et al. | |
| 2012/0110016 A1 | 5/2012 | Phillips | |
| 2012/0166212 A1 | 6/2012 | Campbell | |
| 2012/0215578 A1 | 8/2012 | Swierz et al. | |
| 2012/0239671 A1 | 9/2012 | Chaudhri et al. | |
| 2012/0278102 A1 | 11/2012 | Johnson | |
| 2012/0284056 A1 | 11/2012 | Hofstetter | |
| 2012/0303378 A1 | 11/2012 | Lieberman | |
| 2013/0007020 A1 | 1/2013 | Basu et al. | |
| 2013/0046529 A1 | 2/2013 | Grain et al. | |
| 2013/0124523 A1 | 5/2013 | Rogers et al. | |
| 2013/0159023 A1 | 6/2013 | Srinivas et al. | |
| 2013/0231956 A1 | 9/2013 | Chaudhri et al. | |
| 2013/0238349 A1 | 9/2013 | Sethumadhavan et al. | |
| 2013/0291060 A1 | 10/2013 | Moore | |
| 2013/0297536 A1 | 11/2013 | Mmosni et al. | |
| 2013/0332194 A1 | 12/2013 | DAuria et al. | |
| 2013/0332199 A1 | 12/2013 | Freiwat et al. | |
| 2014/0012738 A1 | 1/2014 | Woo | |
| 2014/0046697 A1 | 2/2014 | Rogers et al. | |
| 2014/0136559 A1 | 5/2014 | Kottaram | |
| 2014/0257842 A1 | 9/2014 | Heinze et al. | |
| 2014/0278832 A1 | 9/2014 | Glavina et al. | |
| 2015/0019463 A1 | 1/2015 | Simard et al. | |
| 2015/0066537 A1 | 3/2015 | Sheffer et al. | |
| 2015/0066539 A1 | 3/2015 | Sheffer et al. | |
| 2016/0048643 A1 | 2/2016 | Woods et al. | |
| 2017/0132314 A1 | 5/2017 | Liu et al. | |

FOREIGN PATENT DOCUMENTS

| | | | |
|---|---|---|---|
| JP | 11219403 | A | 8/1999 |
| JP | 2001290890 | A | 10/2001 |
| JP | 2001325290 | A | 11/2001 |
| JP | 2002318820 | A | 10/2002 |
| JP | 2003263507 | A | 9/2003 |
| JP | 2004280807 | A | 10/2004 |
| JP | 2005309666 | A | 11/2005 |
| JP | 2006107299 | A | 4/2006 |
| JP | 2006164234 | A | 6/2006 |
| JP | 2007193399 | A | 8/2007 |
| JP | 2007323525 | A | 12/2007 |
| JP | 2008204378 | A | 9/2008 |
| JP | 2009193157 | A | 8/2009 |
| JP | 4471736 | B2 | 6/2010 |
| JP | 2010134946 | A | 6/2010 |
| KR | 100750071 | B1 | 8/2007 |
| KR | 10-2009-0050881 | | 5/2009 |
| KR | 1020120004749 | B1 | 1/2012 |
| WO | 2008039880 | A2 | 4/2008 |

OTHER PUBLICATIONS

Korean Intellectual Property Office, ISA, "International Search Report and Written Opinion" in PCT Application No. PCT/US2012/053182, dated Mar. 18, 2013, 12 pages.

ISA/US, "Notification of Transmittal of the International Search Report and the Written Opinion of the International Searching Authority or The Declaration", in PCT Application No. PCT/US2014/012138, datedd Apr. 21, 2014, 7 pages.

The Statistics Calculator, StatPac; Dec. 17, 2003, available from: http//web.archive.org/web/20031217141819/http://stapac.com/statistics-calculator/percents.htm.

A Lynunn, How Elasticsearch calculates significant terms, Jun. 10, 2015, ComperioSearch (Year: 2015).

Bentkus et al., "Confidence Bounds for a Parameter" Sep. 2001 Mathematics Subject Classification.

Feature Selection, Apr. 5, 2016, Wikipedia (Year: 2016).

Natarajan et al., "An Analysis of Clinical Queries in an Electronic Health Record Search Utility" Int. J Med Inforamtics, Jul. 2010.

Rector et al., "Medical-Concept Models and Medical Records: An approach based on GALEN adn PEN PAD" Journal of the American Medical Informatics Association, Volumn 2 No. 1 Jan./Feb. 1995.

Rogue et al., ""Using Electronic Patient Records to Discover Disease Correlations and Stratify Patient Cohorts"" PLoS Computational Biology, Aug. 2011, vol. 7, Issue 8 el 002141.

Mori et al., "What is Mash-up?", A Web 2.0 service construction technique, iNTERNET magazine, Impress Corporation, Apr. 1, 2006, No. 135, with English Translation, 54 pages.

* cited by examiner

Ex. Of Rules for Clustering $M_1(C)$
$M_1(C)$
$M_2(C)$
$M_2(C)$
•
•
•

Set of associated items + mapping based on category

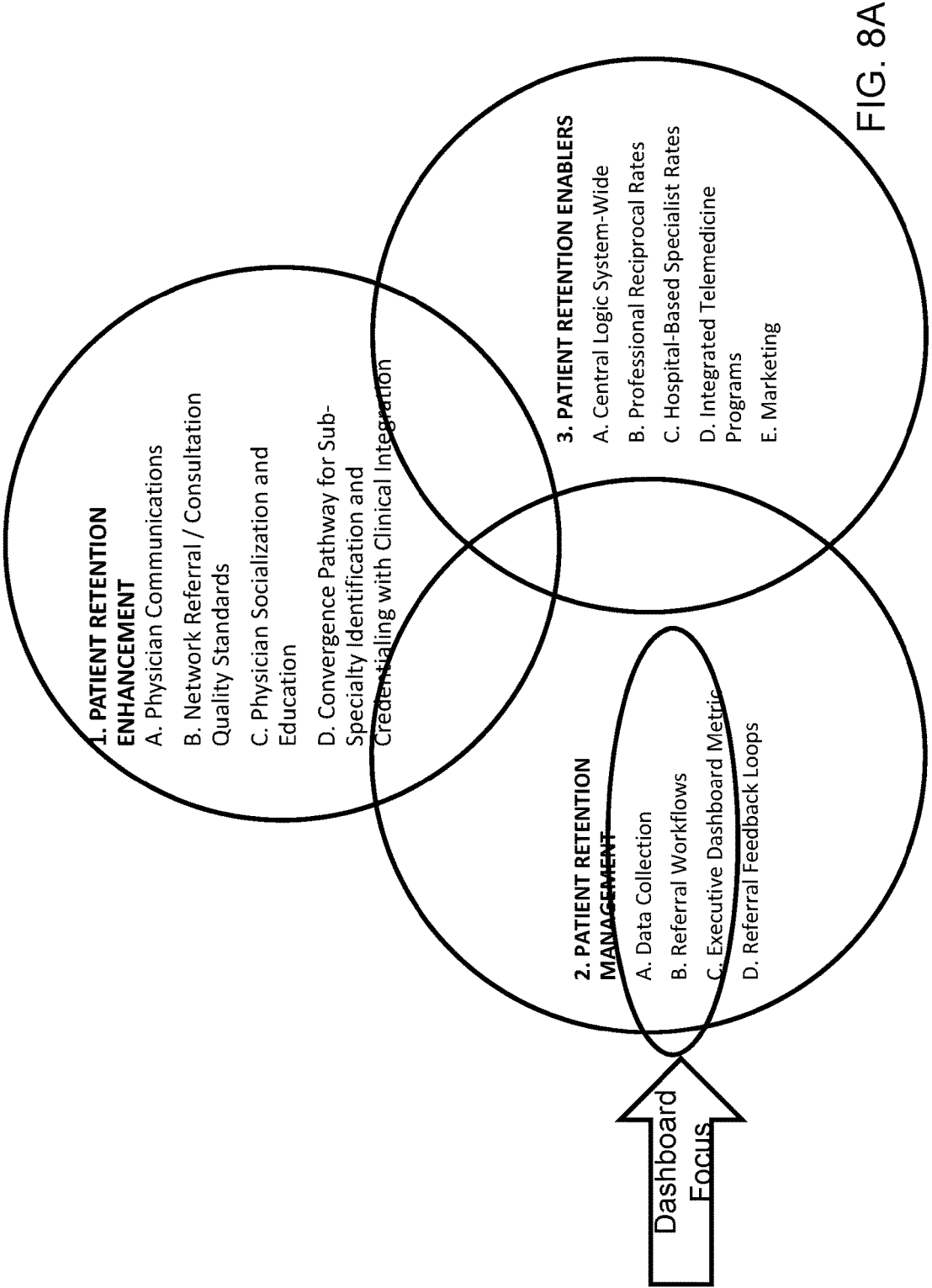

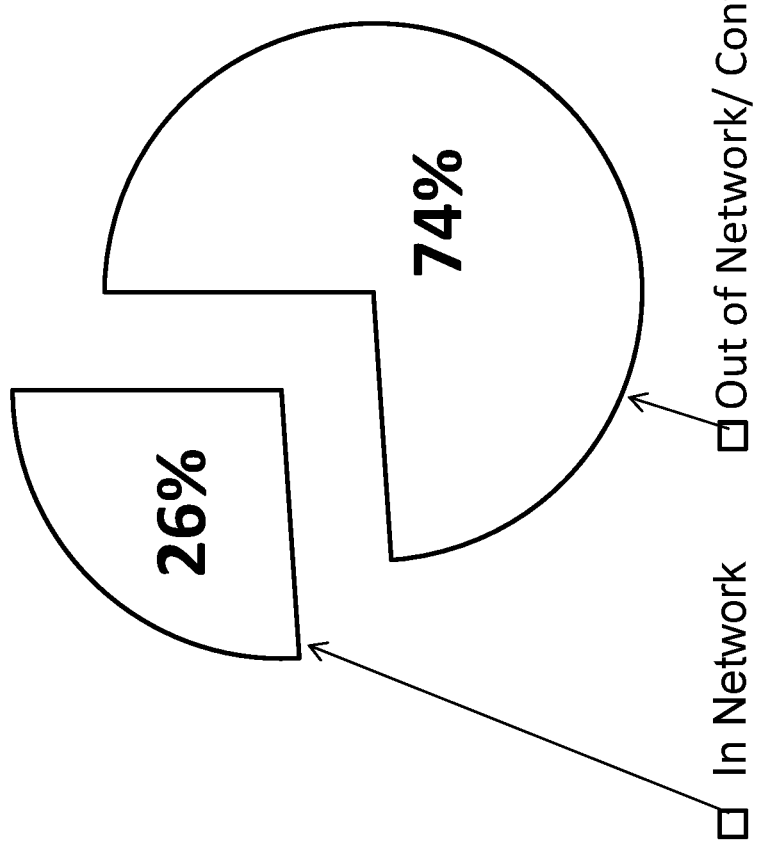

Example - Referral Inferred by the Model but Not Reported in workflow system

Evidence of Colonoscopy Referral

Patient is being referred by PCP for a colo in regards to BRBPR. Is colo ok to schedule and how soon? XXX, GI Surgery Scheduler --Telephone Encounter. 3/23/12

Evidence of the Colonoscopy Performed

COLONOSCOPY REPORT Endoscopist: XXX, MD
Location: Surgecenter of Palo Alto. Referring physician: XXX, MD --Ambulatory Surgery Center. Progress Note. 5/1/12

Fig. 10A

Example - Referral Inferred by the Model but Not Reported

Evidence for Procedure Referral

Can i schedule this patient for an injection at sutter or in-office procedure? ----- Message -----
From: XXX. Sent: 5/10/2012 5:02 PM To: XXX, MD -- Telephone Encounter, 5/10/12

Evidence for Referred Procedure

-- Informed Consent Note for spinal injection, 5/11/12

Example - Epic Referral Reporting Incompletely Represents Referral Activity

- Encounter Note from Referring Physician, XXX, MD. Date: 4/26/12.

YYY is a lovely 73 year old female with memory difficulties who returns for follow up.

...

Plans.
  1) Further work-ups: a) MRI brain w/o gad ASAP to evaluate the right hemiplegia
  ...
  4) PT for the gait training and OT for the right upper extremity monoplegia

- Epic Referral data for this patient: 4/26/12 to 5/31/12

Referral for MRI, Brain. Internal location.
  Date of Referral: 4/26/12. XXX, MD. Referring physician

Fig. 10C

Example – Referral Reporting Incompletely Represents Consulting Activity

Pain Mgmt Clinic Consult Note. Date: 5/29/12

REF PHYS: XXX., MD
CHIEF COMPLAINT: chronic low back pain and left leg pain....
PLAN: ... I offered the patient to perform a series of lumbar epidurals.

Epic Referral data for this patient

Referral for Pain Mgmt Clinic. Internal location.
Date of Referral: 5/1/12. XXX, MD. Referring physician

Fig. 10D

SYSTEMS AND METHODS FOR PATIENT RETENTION IN NETWORK THROUGH REFERRAL ANALYTICS

CROSS REFERENCE TO RELATED APPLICATIONS

This Continuation Application claims priority of U.S. application Ser. No. 13/798,031, filed on Mar. 12, 2013, of the same title, which application is a Non-Provisional Application and claims priority of U.S. Provisional Application No. 61/754,527 filed on Jan. 18, 2013, of the same title, including Appendix A, which applications and appendix are incorporated herein in their entirety by this reference.

Also, U.S. application Ser. No. 13/798,031 is a Continuation-in-Part Application and claims priority of application Ser. No. 13/223,228 filed on Aug. 31, 2011, entitled "Medical Information Navigation Engine (MINE) System", now U.S. Pat. No. 10,176,541 which application claims priority to U.S. Provisional Application No. 61/379,228 filed on Sep. 1, 2010, of the same title, all applications/patents are incorporated herein in their entirety by this reference.

BACKGROUND

The present invention relates generally to a medical information engine, and particularly to management and consolidation of medical information which enables patient retention in a medical network by leveraging analysis of referral practices.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is the number of sources of information, the great amount of information from each source, and consolidation of such information in a manner that renders it meaningful and useful to those in the field in addition to patients. Obviously, this has contributed to increased medical costs and is perhaps largely attributed to the field suffering from an organized solution to better aid the medical professionals, to better aid those requiring more reliable patient history and those requiring more control and access over such information.

Currently, when a patient sees various medical professionals over the years, there is no method for universally tracking recommendations, thoughts, prescriptions, referrals, or diagnosis. This hinders the job of insurance companies in making certain requisite determinations, physicians making decisions that directly impact the health of the patient, and hospitals and other medical institutions that similarly rely but do not have the benefit of the requisite information, not to mention the patient.

For consolidated provider networks it may be possible to centralize a patient's records. However, these records are typically not available outside of the network, and moreover, often the records generated outside of network are often isolated. Patient referrals, thus can cause increased costs for an insurer, and may result in fragmented patient information. In order to reduce operating costs, there is significant pressure to optimize patient retention within a medical network. In order to effectively implement mechanisms for this retention, accurate referral data is required.

It is therefore apparent that an urgent need exists for a medical information navigation engine ("MINE") capable of managing medical information in a manner that is beneficial, reliable, portable, flexible, and efficiently usable to those in the medical field, including patients. A functionality of such a system would be the ability to track patient referrals, and generate models which assist insurers and care providers to track referral practices. Such a MINE should also be capable of reconciling and intent-based clustering of patient data by applying at least one clustering rule to the reconciled medication information, and presenting the clustered reconciled medical information to a user.

SUMMARY

To achieve the foregoing and in accordance with the present invention, systems and methods for managing medical information are provided. In particular, systems and methods for referral analysis using intent-based clustering of medical information is provided.

In one embodiment, a medical information navigation engine ("MINE") is capable of analyzing referral data by inferring referral activity not reported into a referral workflow system utilizing intent-based clustering of medical information. The intent based clustering reconciles received medical data, from a variety of sources, and then clusters the data by applying one or more clustering rules. These rules may include similarity rules, in some embodiments, where distance between a patient attribute and the reconciled is computed. If the distance is below a threshold then the referral can be modeled for.

After the referrals not otherwise reported are inferred, they may be utilized to generate metrics that can be utilized to enhance patient care, and reduce costs. The metrics can be generated by adding the inferred referral activity to reported referral activity to generate a combined referral number, and dividing the reported referral activity by the combined referral number. This calculation may be performed for both in network and out of network referrals in order to distinguish differences in reporting activity. The clustering can also be utilized to identify the type of referral (i.e. radiology) in order to analyze trends, and develop patient retention practices.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIGS. 8A-8C show exemplary diagram for implementing patient retention in a medical network;

FIGS. 9A and 9B show example diagrams for analytics generated by the MINE 112 for patient referrals;

FIGS. 10A-10E show example evidence analyzed by the MINE 112 to generate referral analytics.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "always," "only," "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

I. System Architecture

Figure 1:
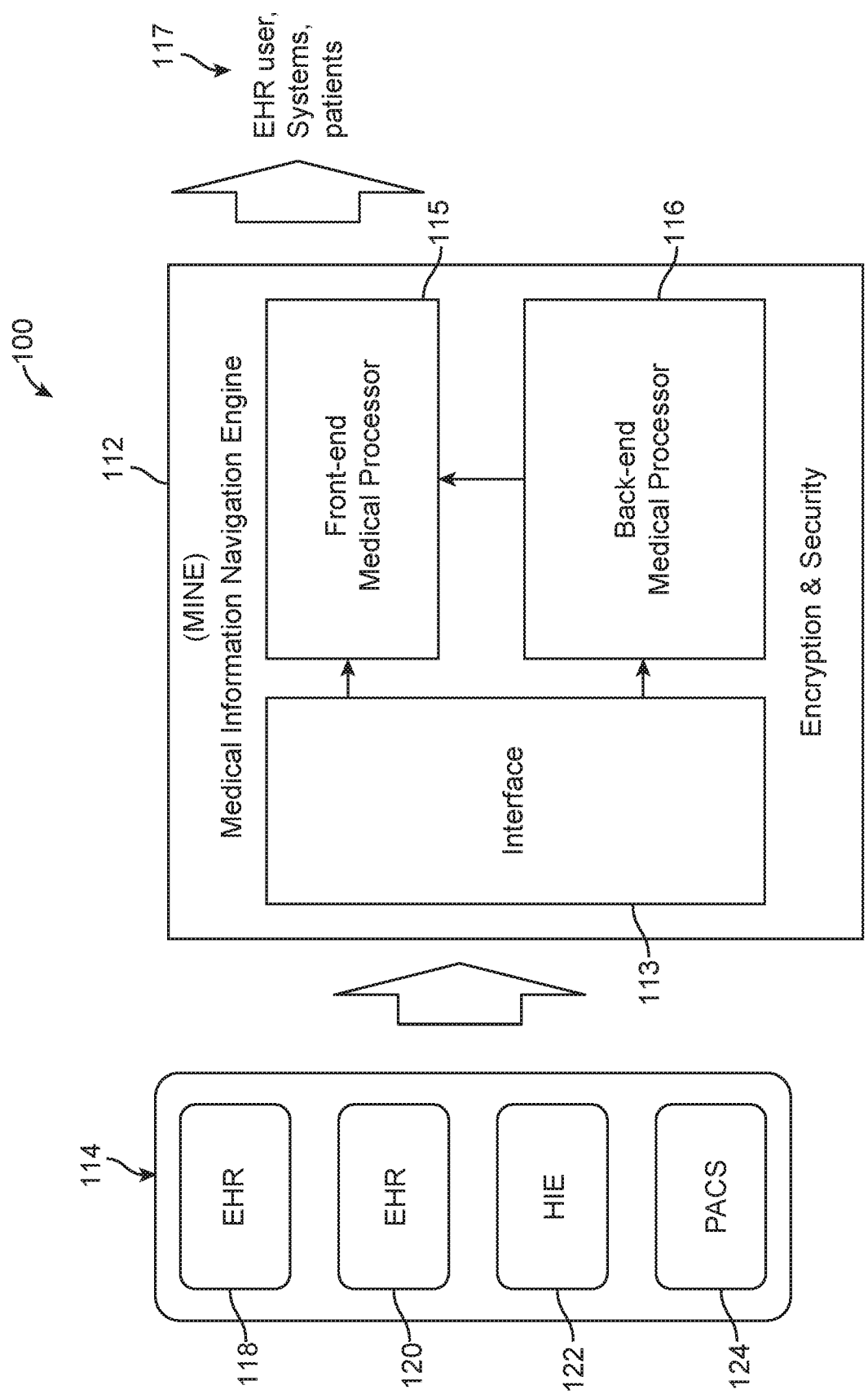
FIG. 1 shows a medical system 100, in accordance with an embodiment of the invention.

Referring now to FIG. 1, medical system 100 is shown, in accordance with some embodiments. The system 100 is shown to include medical source 114, a medical information navigation engine (MINE) 112, and medical information consumers (also referred to herein as "output" or "medical output") 117. The medical source 114 are shown to include one or more electronic health records (EHR) 118 and 120, health information exchange (HIE) 122, and a picture archiving and communication system (PACS) 124. The MINE 112 is shown to include interface 113, a back-end medical processor 116, and a front-end medical processor 115.

"Medical information", as used herein, refers to any health-related information, including but not limited to patient medical records, patient entered information, care team entered information, healthcare device generated information, referral information, and billing information.

The source 114 generally provides various medical information to the MINE 112. For example, the EHRs 118 and 120 each may provide information such as medical records and billing, the HIE 122 may provide information such as medical records, and the PACS 124 may provide information such as diagnostic imaging and reports.

The medical information consumers 117, which may be made of a host of entities or individuals, such as patients, clinics, medical institutions, health organization, and any other medical-related party, use information that is provided by the processor 115 of MINE 112 and that can, by way of example, consist of patients, medical systems, medical organization administrators, medical researchers, and/or EHR users. For example, user-customized processed medical information is provided by the processor 115 to a number of users within the medical information consumers 117. In this case, the processor 115 generates user-customized processed medical information to a plurality of users, with at least a portion of the user-customize processed medical information being provided to each of the users based on the relevancy of the portion being provided of each user's specific function or role and each user's associated security privileges.

The processor 116, in some embodiments, indexes identifies, maps, and consolidates medical information, received from the interface 113, and tags this information, and determines to reconcile the tagged information. In some methods and embodiments, information that is extracted from images is tagged to enhance recall of search queries. Indexing, at least in part, processes document and converts them into formats that allows for quick searching across a large collection of documents.

The information in the MINE 112 is encrypted and secure to ensure privacy of sensitive medical information.

It is understood that the sources 114 of FIG. 1 includes merely some examples of the sources that communicate with the MINE 112 and that other sources, known to those in the field, are contemplated. Similarly, the output 117 may be used by those or entities not discussed herein but that are contemplated and within the scope and spirit of the invention.

The interface 113 serves to receive information that is in various forms, such as but not limited to text, html, CCD, CCR, HL7 and any other type or formatted information. The interface 113 then provides to the processors 115 and 116 information, as needed.

The processor 116 receives some of the medical information that the interface 113 processes and performs certain tasks to process it, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

One aspect of consolidation, reconciliation and de-duplication, generally refers to removing of redundant patient medical records, such as, multiple records for the same individual appearing as though the records are for different individuals or multiple data elements that are recorded similarly but slightly differently in the different sources. In this case, the processor 116 recognizes that the records belong to a single individual or are the same data and just recorded differently and automatically consolidates them. The patient or a user of the system 100 may also manually perform reconciliation. The processor 116 advantageously determines whether or not reconciliation is performed.

The processor 116 outputs the indexed, tagged and reconciled information to the processor 115. The foregoing tasks are a generalization and further details of each are provided below.

Figure 2:
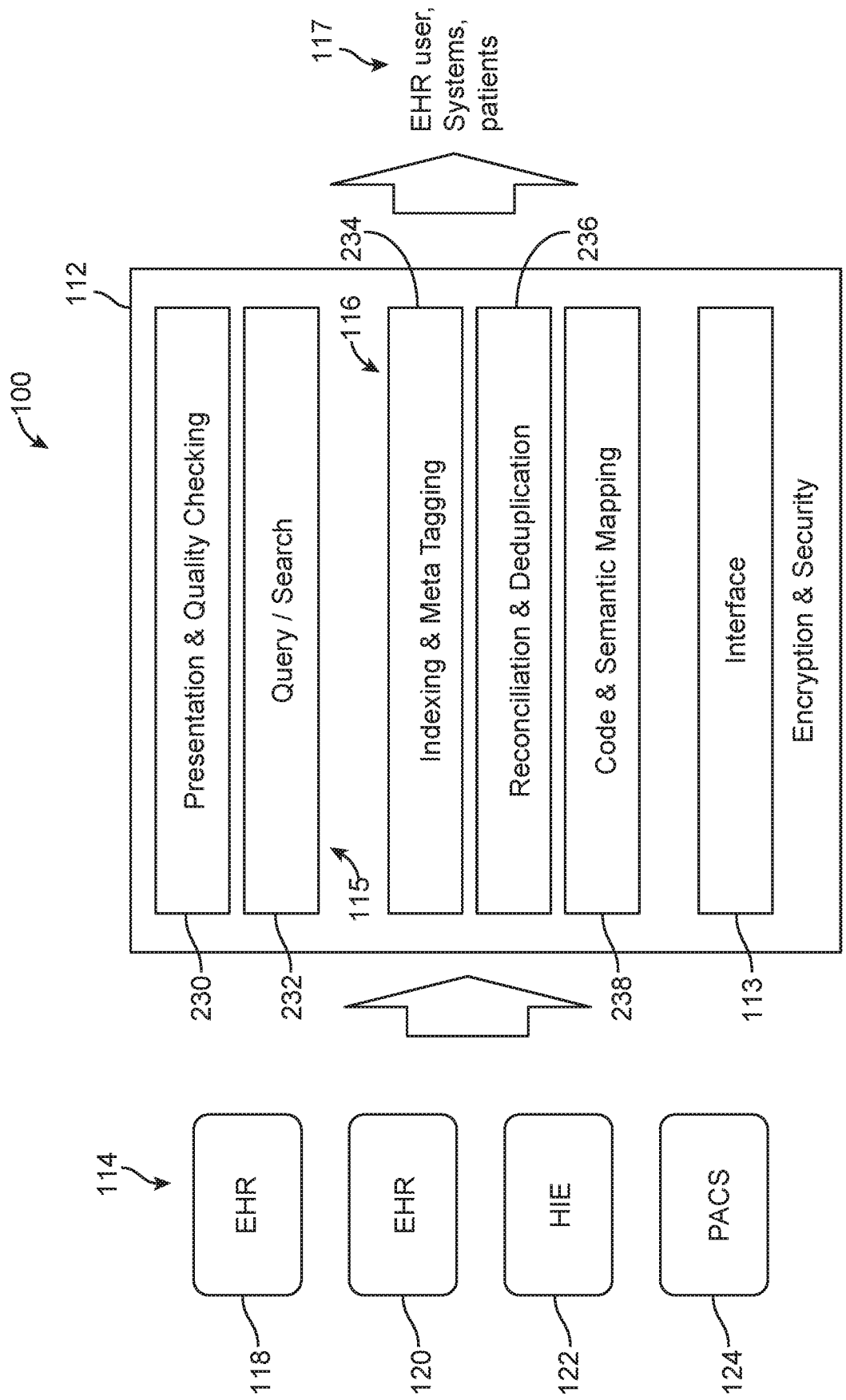
FIG. 2 shows further details of the MINE 112 of FIG. 1, in accordance with an embodiment of the invention.

The processor 115 performs certain tasks on the information provided by the interface 113 and the processor 116, which include query/search 232, and presentation and quality checking 230 (both shown in FIG. 2). The output of the processor 115 is the output of the MINE 112, or output 117.

The MINE 112, through the processor 115, in some embodiments and methods, invites members of a medical care team to join it thereby allowing distributed user-organized care teams.

Querying 232 as performed by the processor 115, is the ability to receive, as input, a free text query, from a user, (i.e., a query without any restrictions on the structure)—and converting the free text query into commands to a medical search engine, such as Medical Lexical Search Engine and the MATRIX (Medical Application Terminology Relationship IndeX) Concept Search Engine, using a sophisticated query processing engine optimized to work with medical queries. The results of the search engine are sent to the presentation display planner—which decides the most relevant presentation given the user's organization and role (e.g. the provider, search query program, a healthcare administrator, a study administrator, and the patient). The presentation discussed below, receives such information. In some embodiments and methods, the medical information or user information is processed to suggest relevant queries.

Search 232, as performed by the processor 115, is built around the concept of ZeroClick Relevance—or the ability to get to all the relevant information an actor in the healthcare system requires by typing in just a single query. The search engine, within the processor 115, performing the search comprises an indexing and searching, as will become apparent shortly. Optionally, search results may be securely embedded into third party programs. In some embodiments, searching involves determining presenting (also referred to herein as "providing") access to specific relevant data based on a search query, the patient, and the user's specific function and/or role and security privileges. A user may be within the output 117 and security privileges are either determined by the MINE 112 or by the patient or both. The information that is uploaded to the MINE 112 by users, such as in output 114 (in some embodiments) is searched by the processor 115. The uploaded information may include information such as but not limited to status posts, records, and images. Such user-uploaded information is routed automatically to the output 117, as needed.

Some aspects of the search are now discussed relevant to an example. Assuming, by way of example, that Dr. Smith, an internal medicine physician, sees a new patient, Joan Sample, who presents with a complaint of chest pain. Joan has brought several continuity-of-care documents (CCDs) and a 600-page pdf file representing of her medical chart. She has seen a cardiologist who uses NextGen's electronic medical record (EMR) and a gastroenterologist who uses eMD's EMR and she has recently visited a local emergency room. Dr. Smith uses the search of the various methods and embodiments of the invention to efficiently assemble the relevant information he needs. Dr. Smith selects Joan Sample as the patient and enters the clinical context "chest pain" in the search bar of a screen presented by the MINE 112 (examples of such screens are shown in subsequent figures herein). He is presented with relevant lab results, such as CKMB, troponin, and amylase; relevant diagnostic results, such as prior electrocardiograms (EKGs) and the most recent chest computed tomography (CT) scan; and all progress notes and consult reports in which concepts relevant to chest pain, like "GERD" and "cardiac stress test", are mentioned. Two distinct types of searches are combined, in accordance with a method and embodiment of the invention, to retrieve information medically relevant to Joan's complaint: 1) Lexical search, where text in the patient record is searched for occurrences of the search term, its variants and synonyms; and 2) Medical concept search, where data that is medically related to the search term is retrieved. Medical concept search finds relevant structured data with standardized codes, such as lab results, and text results, such as progress notes, which include terms medically related to the search term. In Joan's case, a search for "chest pain" returns a CKMB lab result and a reference to the most recent chest CT scan. Accordingly and advantageously, the Lexical and Medical concept search solves Dr. Smith's information overload problem by returning information in the chart most relevant to determining the etiology of Joan's chest pain complaint. Further, in some embodiments, the presentation, discussed shortly, presents a united view of Joan's history by reconciling and de-duplicating data from multiple sources that may be coded and described differently. Redundant data is automatically reconciled even if it is described differently by differently sources.

Presentation 230, as performed by the processor 115, is displaying health information to the requesting user in a way that reduces the number of clicks and maximizes the amount of meaningful information delivered based on the interpreting the intent of the user query.

Quality checking 230, as performed by the processor 115, is checking of the quality of medical information provided by various sources, i.e. source 114, by the patients, structured data, and unstructured data, in a Wiki-like mannered setting whereby the users can help maintain and improve the quality of information displayed. The foregoing tasks, performed by the processor 115, are further described in detail below. Additionally, the users or patients may make comments regarding medical information, in a Wiki-like manner.

In summary, the MINE 112 transacts medical information including the interface 113 receiving medical information from a number of medical sources (such as within the source 114) for processing, identifying, mapping, and consolidating by the medical processor 116, providing access to specific relevant data, based on a user's security privileges, within the identified, mapped, and consolidated medical information, based on user-specific functions or roles, performed by the processor 115, and generating user-customized processed medical information to a number of users, such as within the output 117, with at least a portion of the user-customized processed medical information being provided to each of the users based on its relevancy to each user's specific function or role and each user's associated security privileges.

FIG. 2 shows further details of some embodiments of the system 100, particularly the MINE 112 thereof. That is, the processor 116 is shown to include an indexing and metal tagging module 234, which includes an indexing module and a meta tagging module (both of which are not shown in FIG. 2 in the interest of clarity), which may be a module, as shown in FIG. 2 or two physically separate modules. The processor 116 is further shown to include a reconciliation and de-duplication module 236, which also can be broken out into two modules, a reconciliation module and a de-duplication module, and a code and semantic mapping module 238, which also may be a single module or multiple modules. The modules 234, 236, and 238 communicate with one another.

The processor 115, in some embodiments, includes display and visualization 340 executing on one or more servers 338, which may be any suitable computing engine, similar to the servers 332, including but not limited to PCs or servers. The display 340 is used to construct presentation and display information to users, such as the patient's records, billing information, and other types of medical information. The display 340, in some embodiments, also performs processing of some of the functions of the processor 115.

The foregoing modules may be software programs, executed by a computer or computing engine of suitable sorts, or may be implemented in hardware.

Figure 3:
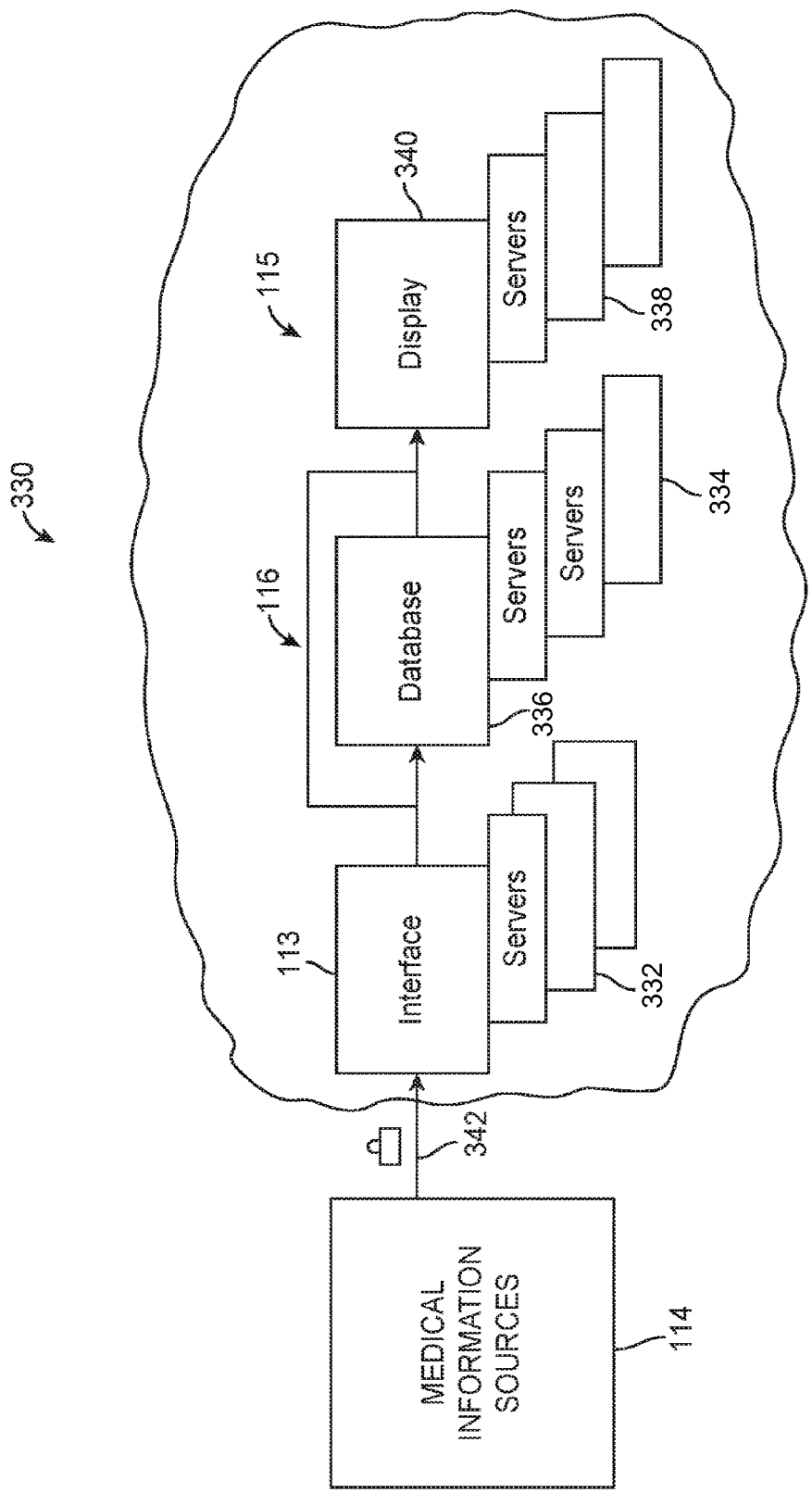
FIG. 3 shows an exemplary embodiment implementing the system 100 using various devices.

FIG. 3 shows an exemplary embodiment implementing the system 100 using various devices. That is, the medical system 330 is analogous to the system 100 and is shown to include the sources 114 coupled to communicate, securely, through the secure communication link 342, to the interface 113. The link 342 may be any suitable communication channel allowing information, of various formats and types, to be transferred to the interface 113 in a secure and encrypted fashion. Exemplary communication channels of which the link 342 is made include the Internet, VPN connections over the Internet, private dedicated digital lines such as T1, T3, E1, E3, SONET, and other fiber optic formats.

The interface 113, in some embodiments, is a software program that executes on one or more servers 332, which can be a server of any kind of suitable computing engine, such as personal computer (PC). The servers 332 receive secure information through the link 342 from the sources 114. The processor 116, in some embodiments, includes database 336 and one or more servers 334, which may be any suitable computing engine, similar to the servers 332, including but not limited to PCs or servers.

The database 336 and servers 334 perform the tasks discussed above relative to the processor 116 and the display 340 and servers 338 perform the tasks discussed above relative to the processor 115 though these processors may and often perform additional tasks related to medical information, some examples of which are presented and discussed below and the rest of which are contemplated and achieve the various advantages, results and functions presented herein.

The processor 115, in some embodiments, includes display and visualization 340 executing on one or more servers 338, which may be any suitable computing engine, similar to the servers 332, including but not limited to PCs or servers. The display 340 is used to construct presentation and display information to users, such as the patient's records, billing information, and other types of medical information. The display 340, in some embodiments, also performs processing of some of the functions of the processor 115.

As shown in FIG. 3, the servers 332 are coupled to the database 336 and the servers 334, and to the display 340 and the servers 338 and the database 336 and servers 334 are coupled to the display 340 and the servers 338.

In some embodiments, the interface 113, servers 332, database 336, servers 334, display 340, and servers 338 are remotely located relative to the sources 114 and in some embodiments, remotely located relative to one another. Further, they are considered a part of the Internet cloud where, performing their tasks in a manner known as "cloud-computing". However, other manner of achieving the functions and advantages of the invention, including various other of implementation, not shown in FIG. 3 or other figures herein and/or not discussed are contemplated.

Figure 4:
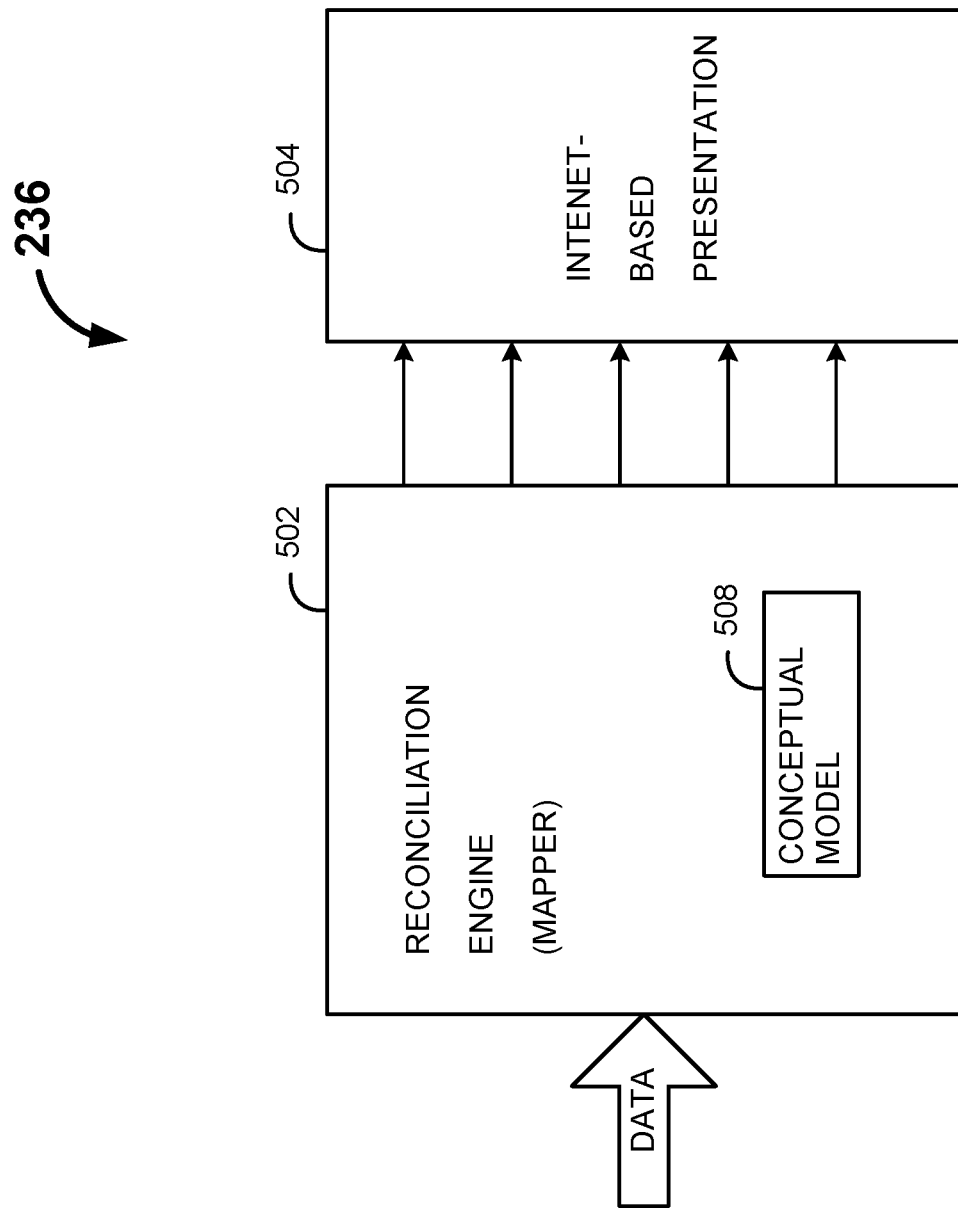
FIG. 4 shows further details of the system 100, in accordance with an embodiment of the invention.

FIG. 4 shows further details of the module 236 of FIG. 2, in accordance with an embodiment of the invention. The module 236 is shown to include a reconciliation engine (also referred to hereinafter as the "mapper") 502 responsive to data 506, which is, at least in part, within the source 114, and is shown to provide reconciled information that is provided to the intent-based presentation block 504.

The engine 502 advantageously learns, through history, ontology, user-input, the type of user, and a host of other factors, similarities between various information from the data 506, defines characteristics thereof, models this information conceptually, pre-selects and sorts information before providing it the block 504 for presentation in the form of a display, or other known types of presentations. Such processing entails the use of various sets of rules, at various stages, as will be evident shortly relative to subsequent figures and discussions.

Presentation by the block 504 is intent-based, that is, the user of the module 236 along with history, and other factors are used to determine the information to be presented. With time, as the engine 502's knowledge of medical information, such as drugs, type of users, diagnosis, the relationship between various diagnosis/diseases relative to each other and relative to various medications, and other information, increases, the information presented by 504 becomes increasingly intent-based.

The engine 502 is shown to include a conceptual model block 508, which conceptually models the data 506, such as to determine similarities, an example of which is provided and discussed in subsequent figures.

Figure 5:
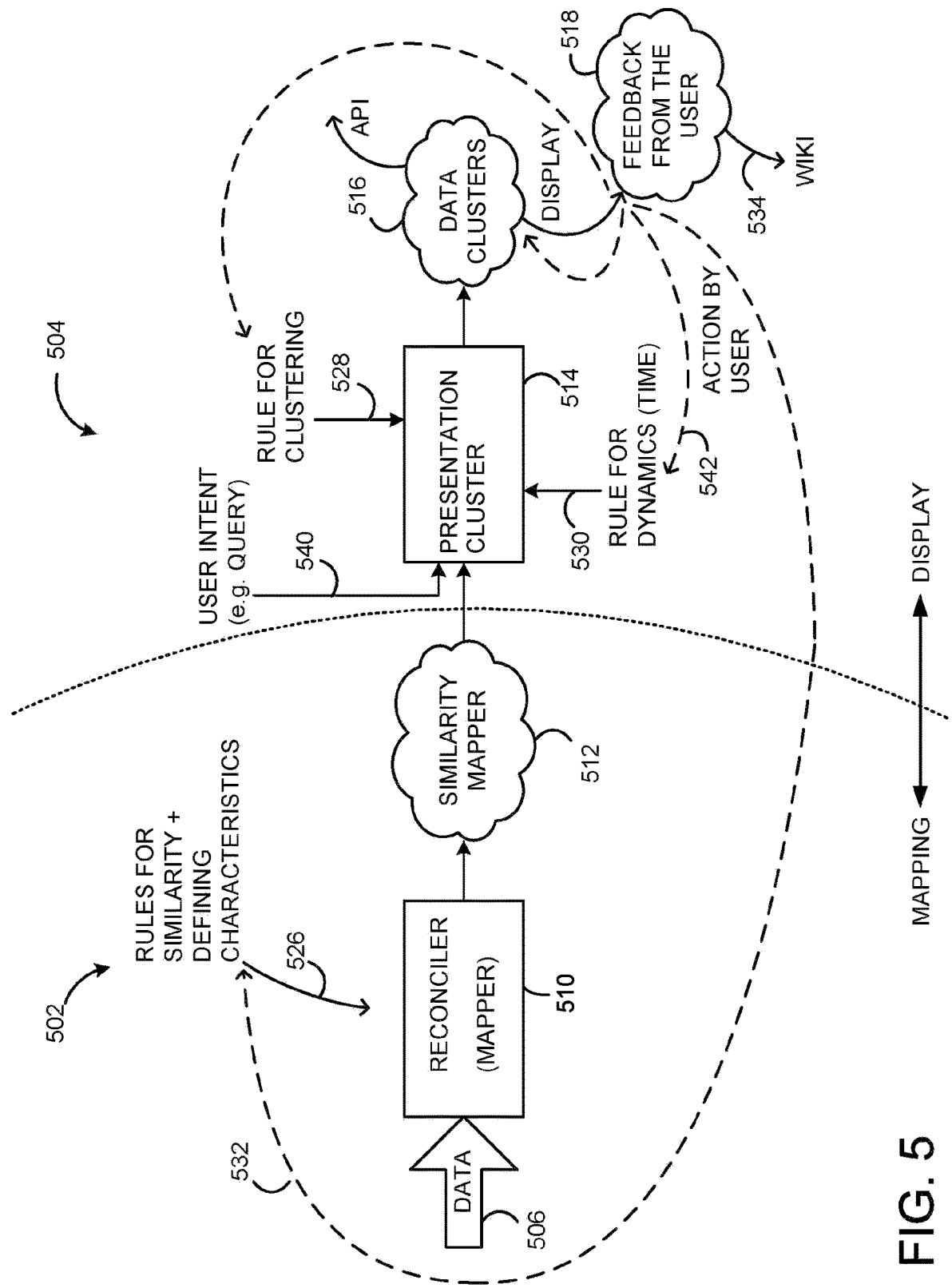
FIG. 5 shows further details of the engine 502 and the block 504 of FIG. 4.

FIG. 5 shows further details of the engine 502 and the block 504 of FIG. 4. The engine 502 is shown to include a reconciler block 510 that receives data 506 and a similarity mapper 512, which generally performs the tasks of the conceptual model block 508 in FIG. 4. The block 504 is shown to include a presentation cluster block 514, which is shown to information from the mapper 512, and a data cluster 516.

A set of similarity rules 526, which identify similarities of various types of information, and define characteristics thereof, is shown being utilized by the reconciler 510. The rules 526 are applied to the data 506 to identify similar concepts, which unlike prior art techniques, is not to look for matches and rather to correlate information based on concepts. Through feedback 532 from users 518, this becomes a learned process with improved and more sophisticated conceptual similarity detection. The similarity mapper 512 maps the reconciled information, generated by the reconciler 510.

Another set of rules, namely, a set of clustering rules 528, is provided to the presentation cluster block 514 for determining which information, if any, to cluster or group. The block 514 also receives as input, user intent query 540, from a user, and applies the rules 528 to the latter. The rules 528 are used by the block 514 to group information received from the mapper 512, based on the user intent query 540, and in the process additional apply a set of dynamics (time) rules 530 thereto. The rules 530 serve to identify what is to be looked at to find what information has been changed over time. In this respect, feedback from the user, through 542, is utilized. Similarly, the rules 528 utilize feedback from the user. Additionally, feedback from the user is utilized, at 534, to accumulate concept-based information and definitions in a Wiki-style fashion.

The presentation cluster block 514 generates output data clusters 516. The cluster 516 information may be displayed and/or presented in other manners, such as with an Application Programming Interface (API), and it further may receive user feedback and use the same to further refine rules for clustering and similarity mappings.

The rules 526, 528, and 530 are independent of one another in some embodiments of the invention. In other embodiments, information flows there between. Advantageously, these rules, partly because they are applied at different stages in the processing of the data 506, allow for a learned and conceptualized process as opposed to a hard decision. For example, in current techniques, where only one set of rules are utilized early on in the processing of the data, a hard decision is made with no flexibility to alter this decision thereby increasing the risk of mis-categorization and/or identification of relevant information. In contrast, thereto, the different sets of rules of the embodiment of FIG. 5, breakdown categories, such as similarity, display, and history, allows configuration of various aspects thereof.

By way of example, in prior art techniques, where the data is regarding electronic devices and a cell phone is to be identified, where the single set of rules, made early on in the process, is based on the lack of a keyboard, and a central processing unit, the device may be erroneously identified as an electronic tablet, with no recourse. Whereas, the embodiment of FIG. 5 allows for progressive learning of various attributes of the device by, for example, using the above exemplary rules as the rules 526 but based on the rules 530 and 528, introducing attributes, such as size of the device, that allow for a more accurate identification of the device. And further, due to the user-feedback and query, allow for dynamically altering the rules.

Use of various rules, such as rules 526, 528, and 530, at various stages of processing, allows flexibility in applying the rules to achieve greater accuracy of clustering. In medical applications in particular, information is oftentimes duplicated for various reasons, such as lack of standardization of names of medications, shorthand identification of information, and a slew of other reasons. In this regard, flexibility of applying rules is vital. While three sets of rules are shown in the figures and discussed herein relative to various embodiments, it is understand that a different number of rules may be employed.

II. Medical Information Management

Figure 6:
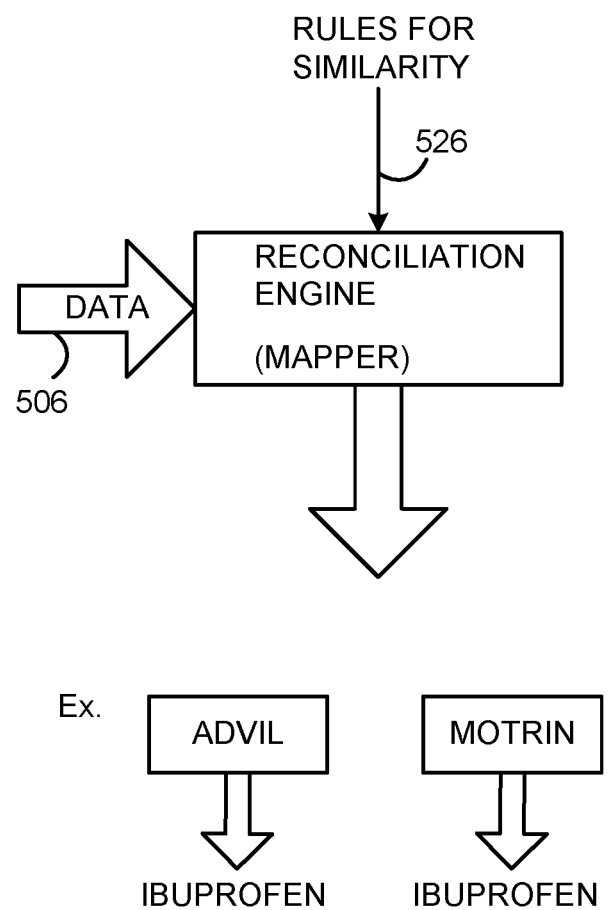
FIGS. 6 and 7 each show examples of applying the rules 526, and 528 and 530, to the data 506 to yield certain beneficial results.
Figure 7:
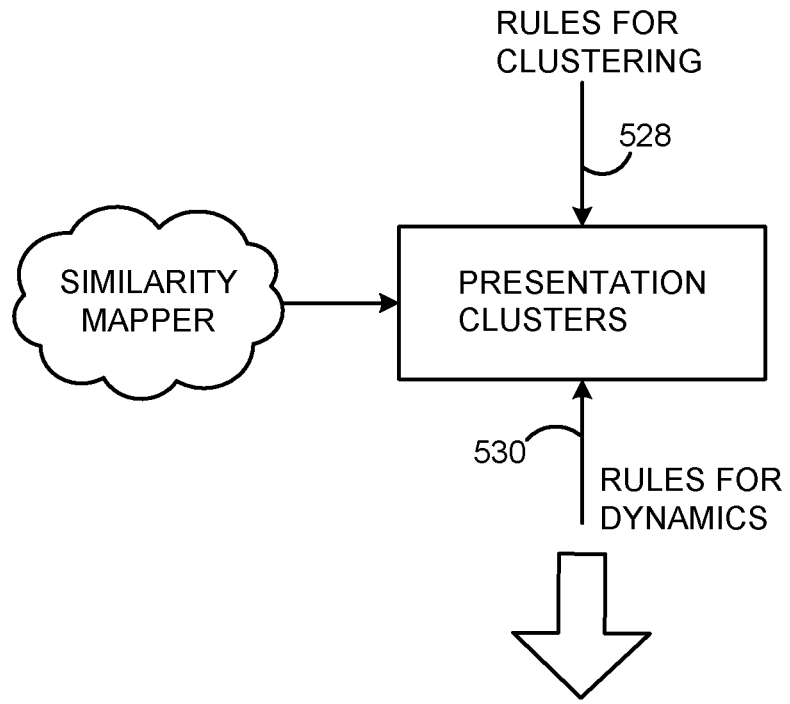

For a better understanding of the flexibility the rules of FIGS. 5-7 offer, an example is now presented. Suppose the data 506 carries medical information for which a particular condition, e.g. diabetes, is to be detected. Rule 526 allows for a similarity between lab results and "diabetes" to be identified but that is nearly where the application of rule 526 ends until further information is known and extracted later in the processing of the data 506. Namely, when rule 528 is applied to the outcome identified by Rule 526, the lab results are crawled or inspected for "diabetes" or another identifier for "diabetes". Additionally, the presence of various relevant labs is detected and the association between the presence of the labs and the problem of diabetes and perhaps, hemoglobin A1c (a measure of average blood glucose concentration over the past 30 to 120 days, used in the diagnosis and treatment of diabetes) is made. Next, the rule 530 is applied to the outcome of the application of rule 528 where patient data is used or a correlation between a problem and a treatment for a large percent of the patient population is made. Specifically, the percentage of patients with diabetes is detected. The parameter of time allows for the latter detection, otherwise, for example, at the application of rule 526 or even rule 528, a large patient base could not have been correlated.

The user input at 540 and the user feedback at 518 all help in the clustering of data. At the application of rule 526, a determination is made as to how things are similar until a user asks about the similarity after which a more educated application of rules is performed. Thus, no decision is made until the end or at the output of the block 514, in real-time.

During the application of rule 526, the system is informed of key parameters but not how to put the data together. Then, during the application of the rule 528, the system is informed of how to put the data together (cluster) by aligning the data in a particular manner. Application of rule 530 determines how things change over time, or not, but not what the correlation or similarity actually is, which is generally done through the rule 528. Part of the reason for splitting the rules is to delay decision-making as long as possible in an effort to cleverly use more information, such as that provided by the user, for an increasingly accurate finding.

The outcome of the data cluster 516 can be transmitted to another processor, system, user, or any other entity.

Another example of the manner rules are employed, outside of the medical community, is for example, in determining parameters of hair where rule 526 is used to look for length of hair and rule 528 uses the outcome of the length of hair to further determine alopecia as compared with normal hair growth. Rule 530 may then be used to determine a percentage of a demographic that has experienced baldness. Further examples of the application of these rules is shown and discussed relative to FIGS. 6-11.

As with the blocks of the MINE 112 of FIG. 1, it is understood that the blocks shown in FIG. 5, such as block 510 and 514, and 516 may be independently a machine and/or processor or a part of a machine and/or processor. They may alternatively, be carried out in software programs.

FIGS. 6 and 7 each show examples of applying the rules 526, and 528 and 530, to the data 506 to yield certain beneficial results. In FIG. 6, rule 526 is applied to the data 506 to identify the medication named "Advil" as an "Ibuprofen". Similarly, "Motrin" is identified as Ibuprofen, therefore, allowing more flexibility to a patient and a medical professional in deciding to use these drugs. Rules for similarity specific what characteristics need to be looked at to determine similarity of an object to another object.

Using the same example, rules 528 and 530 may be applied to the outcome of the rule 526 to the data 506 to determine other information based on the intent of the user. For example, the dosage of Ibuprofen, from all sources, even those with other ingredients, may be determined by applying rule 528, after applying rule 526 such that the outcome of rule 526 detects Ibuprofen types of medications and rule 528 narrows the detection to those with a threshold dosage.

FIG. 7 shows an application of the rules 528 and 530 where a set of associated terms, m1(c), has been identified and another set of associated items, m2(c), has been identified. For example m1(c) is one medication, m2(c) is another medication and "c" are particular characteristics of each medication such as, but not limited to, brand name, generic name, dosage, prescription instructions (sig), prescription date, and start date. Rules for dynamics, rule 526, is the time base characteristics. Rules for clustering, rules 528, would be probability of matches of other characteristics. For example, for a given medication such as oral contraceptive pills (OCPs), the rules of dosage might be ignored such that different prescriptions with different doses would be considered the same for clustering purposes. In this example, the use of oral contraceptive medications at all dosages is contraindicated for women with a genetic predisposition or other risk factors associated with thrombotic events (e.g., venous thromboembolism). Another medication where dosage might be very important to outcomes would not be clustered together if the dosage were different. For example, Warfarin, a medication commonly used to prevent blood clotting, has a very narrow therapeutic window and its metabolism widely varies among individuals. The dosage of Warfarin is highly correlated to outcomes of interest. Physicians routinely prescribe different dosages of Warfarin to treat or prevent thrombotic events or predisposing conditions such as pulmonary embolism or atrial fibrillation.

For further clarification, in the example of Advil and Ibuprofen, if the intent is to investigate whether the current dosage of Ibuprofen is too high, all sources of ibuprofen (even those with other ingredients) are better to be identified, in which case the set m1(c) may represent all sources. The date may also be an indicator, such as the last day or week this medication was prescribed or consumed and may accordingly be a part of the set, m2(c). In contrast, if contributors to (or indicators of) of a chronic condition is the intent, a longer history (months, years) and the chronic condition itself would be "related" despite low "similarity". Thus, through the flexibility of the application of various rules, such as rules 526, 528, and 530, there can be different ways of displaying information, from the data clusters 516, about a concept under different intents.

By way of further explanation, the rules 528 are used to determine what is considered inside the cluster and the rules 530 is how things in the cluster change over time. Though, in other embodiments, other types of rules are anticipated and other numbers of rules are anticipated. Using the Advil/Ibuprofen example above, the rules 528 are used to determine whether other medicines belong in the display cluster, for instance if they contain Ibuprofen but they also contain other things (such as sleep aid, Comtrex) that may or may not "belong" in the display cluster. The embodiment of FIG. 5 advantageously learns whether they "belong" or not. Through the rule 530, the Ibuprofen cluster might emphasize recent events (past week) in the ranking. Other clusters may interact differently with time.

Figure 11:
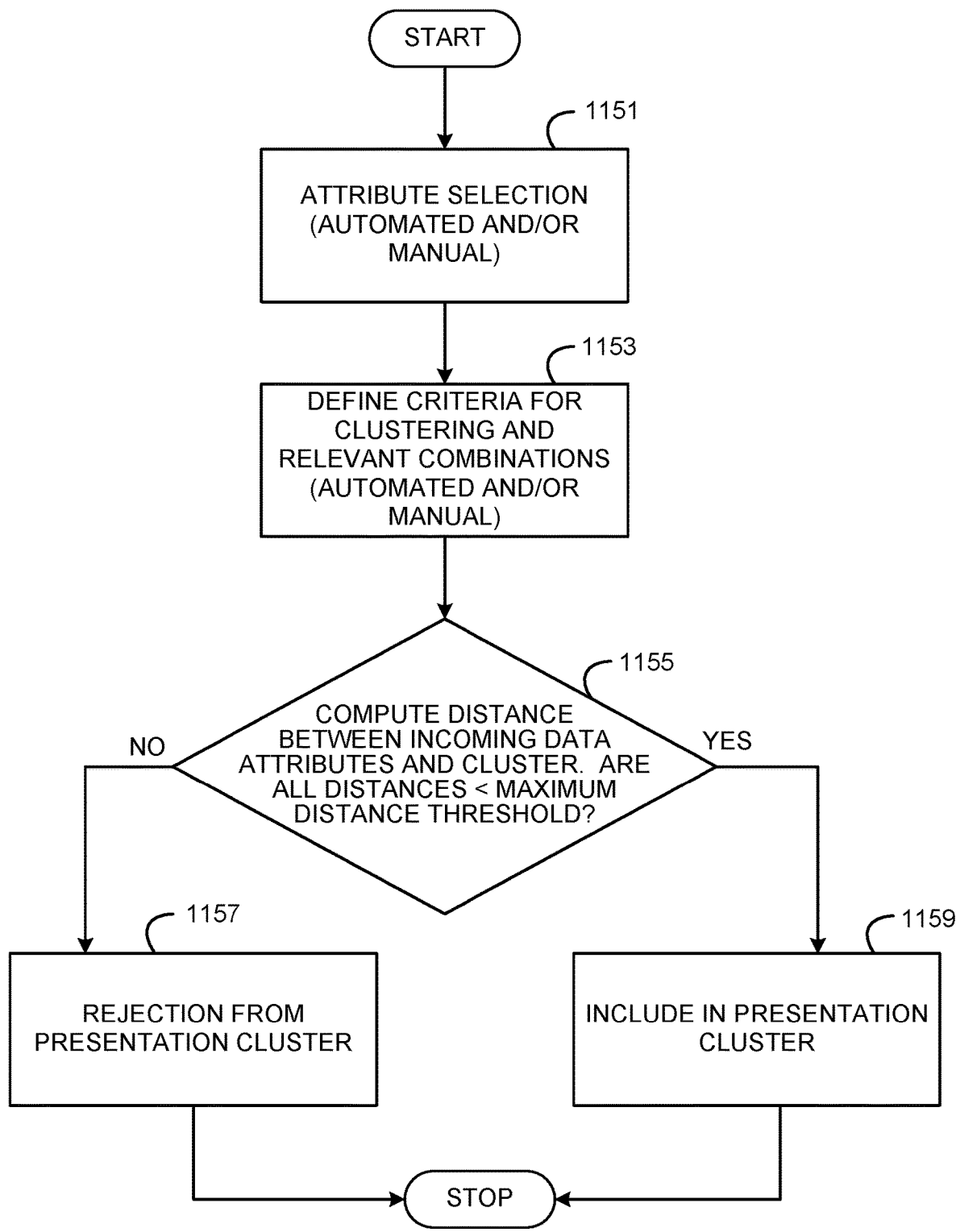
FIG. 11 shows a flow chart of the steps performed by the block 504 of FIG. 5 in applying the rules therein, in accordance with an exemplary method of applying intent-based clustering and display to the data 506 of FIG. 5.

FIG. 11 shows a flow chart of the steps performed by the block 514 of FIG. 5 in applying the rules therein, in accordance with an exemplary method of applying intent-based clustering and display to the data 506 of FIG. 5.

In FIG. 11, at step 1151, an automatic or manual, or a combination, of attribute selection is performed by applying rules 526 and 528, in accordance with a method and embodiment of the invention. Accordingly, attributes to be included in clustering are selected. For example, for a presentation of medications, several attributes might be included. To present results to a user, another machine, processor or the like, for a medication history intent, medication brand name, generic name, coding system, drug code, and ingredient might be selected. This may be done by a user, manually, or automatically by the block 514, in an exemplary embodiment of the invention.

Next, at step 1153, the criteria for clustering relevant combinations is defined, manually, automatically or using a combination thereof. The matching criteria for each of these attributes are defined as a maximum distance along with an appropriate definition of distance. Examples of "maximum match distance" are "exact match", "close match", "loose match" or distance<x where x is an appropriate maximum distance. Examples of distance measures are numerical difference, any edit distance, semantic distance, abstract distance along an ontology or graph, etc. Rules for relevant combinations of the selected attributes are also defined during this step. In some methods and embodiments, attributes can be combined to create a composite threshold that the data 506 can be measured against. With reference to the medication history intent presented hereinabove, all medications in the patient history that are close matches on brand name or generic name might be included, along with exact semantic matches on a particular drug ingredient or exact numerical matches on a group of related drug codes.

Next, at 1155, the distance between the data 506's attributes and cluster is computed. For example, it is determined whether all distances are less than the maximum distance threshold and if so, the cluster is updated to include such data in the presentation, at step 1159, otherwise, step 1157, such data is rejected (not included) in the cluster.

III. Patient Retention in Network

Figure 8B:
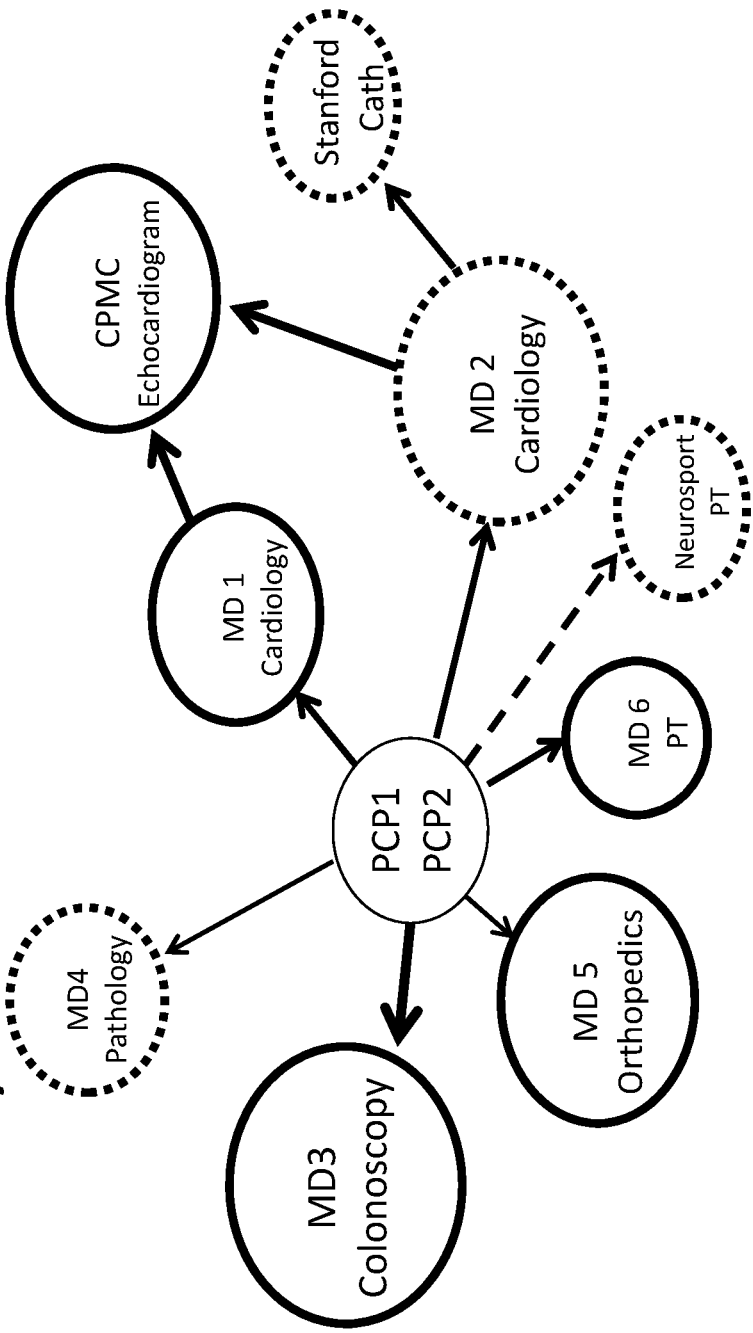
Figure 8C:
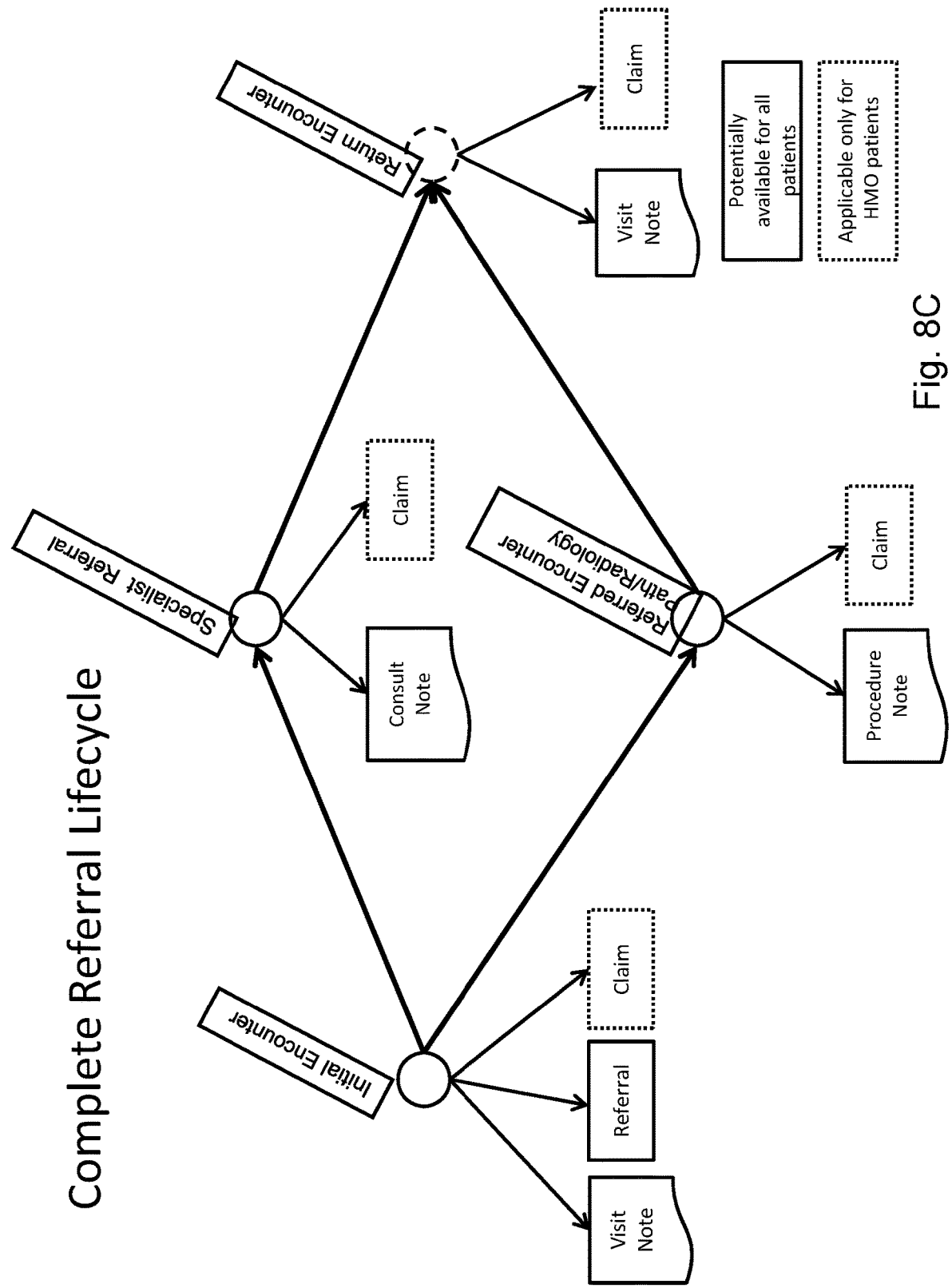

Now that the mechanisms of the MINE 112 have been described in detail, attention should be turned to FIGS. 8A-8C, which discloses means for patient retention through referral analytics and management. The MINE 112 provides the ability to track patient referrals in a manner which may guide practitioners to refer patients in network, and can provide tools for targeting physician education and training on referral practices.

Medical foundations refer substantial patient care outside the Medical Network where equal or superior care is available within the network. These referrals are often uncoordinated and not uniformly reported using existing stacking systems. For most medical providers, it is not clear where these patients are referred or for what reason(s) and the related costs. To ensure affordable, quality care and positive patient experience better referral analytics are desired.

FIG. 8A illustrates that the optimization of patient retention in network relies upon three core areas: 1) patient retention enhancement, 2) patient retention management, and 3) enablers of patient retention. The first category of retention optimization relies upon medical network procedures and education in order to increase patient retention. This is well known, but in order to effectively implement these actions, retention analytics, including referral analytics, are desirable. For example, a procedure for placing quality standards for referrals outside of network may not be effective if the practice area rarely engages in referral practices. In a similar manner, patient retention enablers, such as marketing, central logic systems, and set payment rates enable the retention of patients through affordability and quality of care.

As previously noted, in order to drive enablers to enhance patient retention, patient retention management systems are employed. These systems collect data, generate referral analytics, and otherwise compile and analyze relevant data. The MINE 112 is a particularly powerful tool capable of performing many of these activities.

Moving to FIG. 8B, a physician referral network is illustrated, for context. The goal of any patient referral optimization is to ensure the best patient experience, outcomes and cost. This illustration provides a representative example of what a typical physician referral network may look like, and relative costs associated with the various providers.

FIG. 8C provides an example diagram for a complete referral lifecycle. In this example, a patient has an initial encounter which yields a visit note, a referral and a claim. The referral may be for a specialist or an internal referred encounter. A procedure note or consult note are generated from this interaction. A return encounter is then made, with the generation of another visit note. These records of the encounter may be utilized by the MINE 112 to determine referral activity in ways currently not possible without manual review of each note.

The MINE 112 is able to analyze all referral data to establish an analytical dashboard that provides benchmarking, outcome measures, and enables knowledge driven care. Existing referral workflow systems (i.e. Epic, etc.) only have the ability to report, track and manage referrals if entered. Currently, most referral data is undefined, untrackable and unmanageable, thus making referral workflow systems inefficient. The MINE 112 is capable of picking out the referral data in a manageable form for consumption by the referral workflow systems. With more robust referral data, these referral workflow systems will be able to assist in the development of strategies that optimize access, continuity of care, resource management, affordability, quality, and patient/physician satisfaction.

The disclosed system may then utilize the referral data to generate one or more metrics of compliance by physicians to preferred referral reporting. An example of such a metric is defined by Formula A:

$$\text{Formula } A = \frac{\text{Number of in network referrals reported in the workflow system}}{\text{Total number of in network referrals}}$$

Further, a second metric can be computed which reveals opportunities for improvement of out of network reporting. An example of such a metric is defined by Formula B:

$$\text{Formula } B = \frac{\text{Number of out of network referrals reported in the workflow system}}{\text{Total number of out of network referrals}}$$

The denominator values for these metrics necessitate the usage of the MINE 112 to scour patient records in order to capture all incidences where a referral is given. In order to ensure complete capture of referrals, the MINE 112 data was compared to auditing data. The results of these comparisons are provided in Table 1.

TABLE 1

Analytics of referral versus internal Audit

| Method | Referral entries in workflow system | Inferred referrals not already captured | Total | Formula B results |
|---|---|---|---|---|
| MINE Analysis | 256 | 173 | 429 | 60% |
| Internal Audit | 218 | 131 | 349 | 62% |

As can be seen, given similar samples, the results of the automated MINE 112 modeling of referrals is statistically similar to the results of a costly and time consuming audit. Also striking, is that the referral reporting practices differ significantly when it is an in network, HMO style, practice, as compared to an out of network, PPO style arrangement. Table 2 provides the referral reporting rates for these two scenarios:

TABLE 2

Analytics of referral reporting for in network versus out of network

| Method | Referral entries in workflow system | Inferred referrals not already captured | Total | Results |
|---|---|---|---|---|
| In network (Formula A) | 29,456 | 9,542 | 38,998 | 76% |
| Out of network (Formula B) | 13,365 | 9,479 | 22,844 | 59% |

Figure 9A:
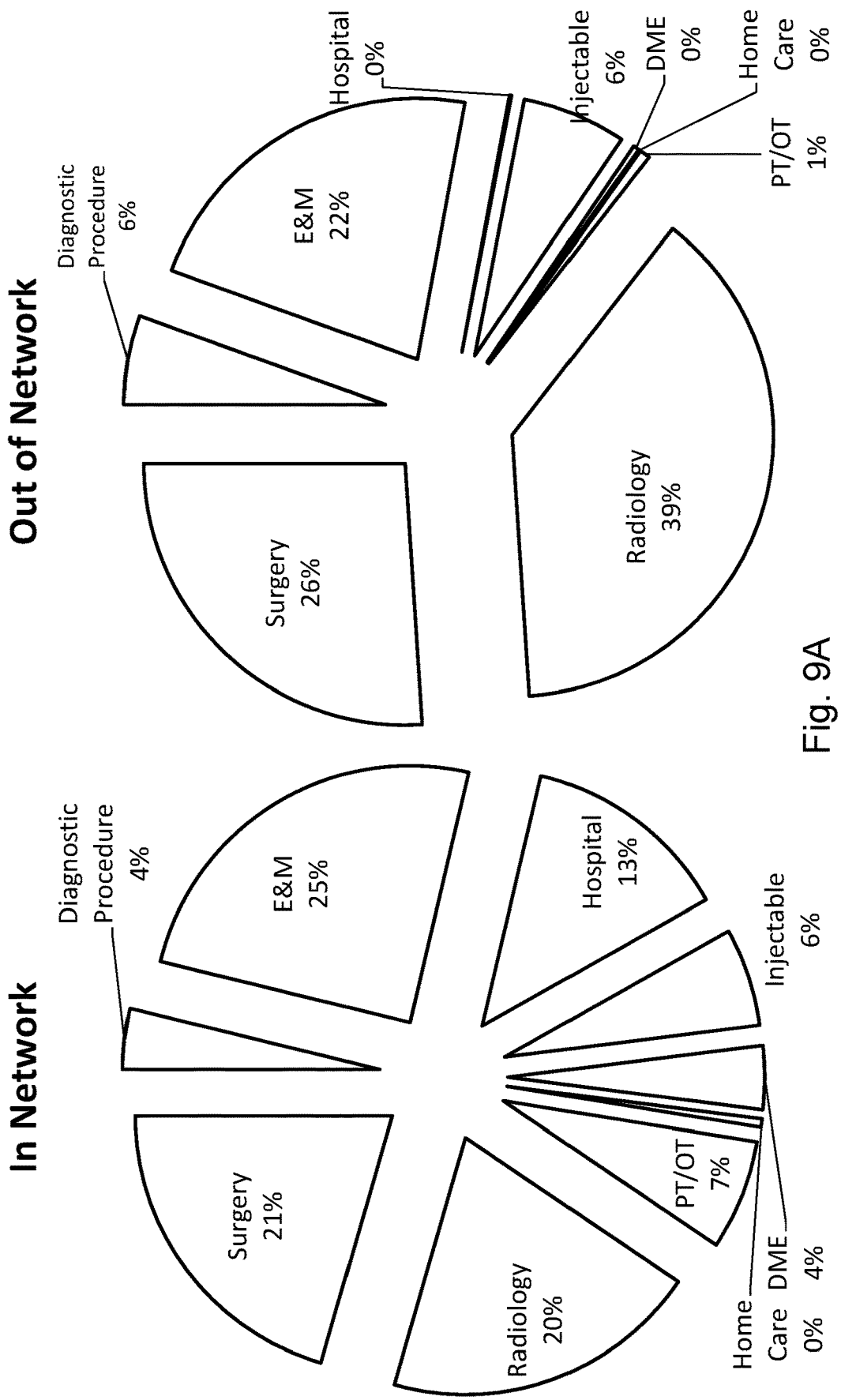

The MINE 112 is also able to utilize its analytical capabilities to pinpoint the distribution of referral services. FIG. 9A provides breakdowns of referral types. Interestingly, the referral distributions have significant differences between in network and out of network referrals. For example, radiology and surgery are referred more frequently when out of network, and hospital and physical therapy is more often referred in network.

FIG. 9B provides a graph illustrating where referrals were located when not in the referral workflow system. The overwhelming majority of these referrals were sent out of network, which on a whole is more costly, and does not deliver a higher level of care. For this very reason, the capture of un-reported referral data is critical to the control over health care costs, and the optimization of patient retention through better outcomes at lower costs.

Lastly, while the architecture of the MINE 112, and the analytics performed to capture referral data that is otherwise not reported has been disclosed in considerable detail, specific examples of referral modeling are helpful for further clarification. FIGS. 10A-10E provide such examples.

Figure 10B:

For instance, in FIGS. 10A and 10B, physician notes can be analyzed for a specific procedure referral, even when the referral has not been reported into a referral workflow system. In contrast, FIGS. 10C and 10D provide an instance where referral activity is being reported in the workflow system (MRI referral) but the physician's notes provide a more complete story (referral is also for occupational therapy).

Figure 10E:
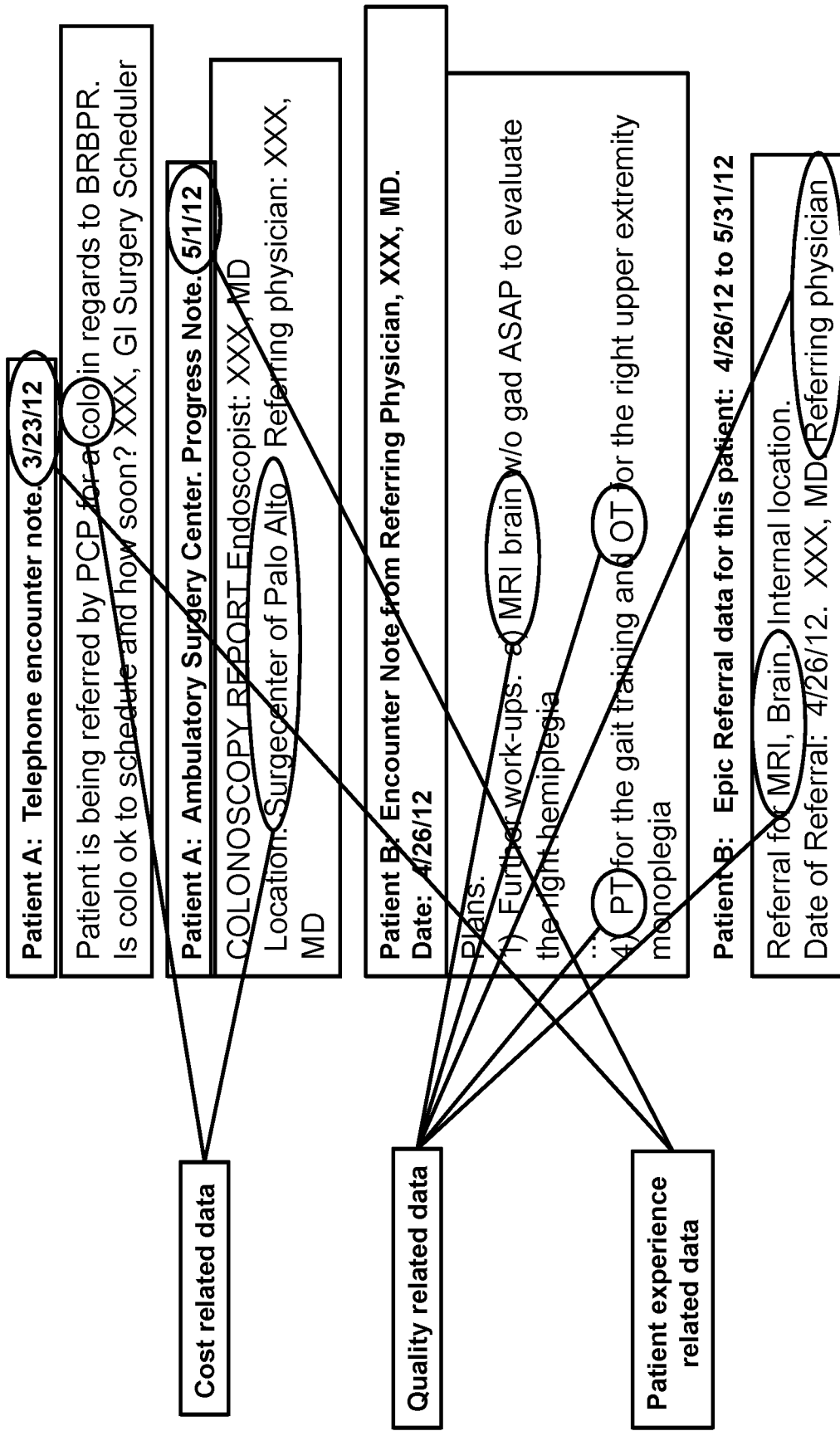

FIG. 10E provides an example of which data is deemed relevant for some embodiment of the MINE 112 as part of the analysis. This includes cost data, quality data, and patient experience data.

While this invention has been described in terms of several embodiments, there are alterations, modifications, permutations, and substitute equivalents, which fall within the scope of this invention. Hence, it should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A computer-implemented method for electronic referral analysis, the method implemented by a medical information navigation engine ("MINE") including an interface server, a front-end server, and a back-end server, the method comprising:

receiving, by the interface server via at least one secure communication link, medical information from a plurality of medical data sources, the medical information including visit-note data and reported-referral data, the medical information received in different formats;

reformatting, by the back-end server, the medical information by converting the different formats into a single format that facilitates reconciling and de-duplicating of the medical information;

transmitting, by the interface server, the reformatted medical information to a database in encrypted form, the database configured to store the reformatted and encrypted medical information;

retrieving, by the back-end server from the database, the reformatted and encrypted medical information;

building, by the back-end server executing a reconciliation engine, an intent-based clustering model by applying a set of rules to the retrieved medical information, wherein the intent-based clustering model is configured to identify one or more referrals within the retrieved medical information and other retrieved medical information, and wherein applying the set of rules comprises:

(i) identifying one or more similarities within the retrieved medical information and defining characteristics of the retrieved medical information by applying at least one first rule of the set of rules to the retrieved medical information, wherein the at least one first rule is configured to learn to detect similarities using first feedback data associated with a plurality of medical information received by the MINE, thereby refining the at least one first rule, ii) clustering the retrieved medical information into one or more groups by applying at least one second rule of the set of rules to the identified one or more similarities, wherein the at least one second rule is configured to learn to detect clusters using second feedback data associated with the plurality of medical information received by the MINE, thereby refining the at least one second rule, and (iii) identifying information within the retrieved medical information that has changed over time by applying at least one third rule of the set of rules to the one or more groups, wherein the at least one third rule is configured to learn to detect changes over time using third feedback data associated with the plurality of medical information received by the MINE, thereby refining the at least one third rule;

inferring, by the back-end server based on the application of the intent-based clustering model to the retrieved medical information, unreported referrals, the unreported referrals comprising instances in which a referral of the one or more referrals detected by the intent-based clustering model does not appear in the reported-referral data;

generating, by the front-end server, metrics by (i) adding reported referral activity in the reported-referral data to the inferred unreported referrals to generate a combined referral number and (ii) dividing the reported referral activity by the combined referral number; and displaying, by the front-end server, an analytical dashboard on a user interface of a user computing device, the analytical dashboard displaying the generated metrics including one or more charts.

2. The method of claim 1 wherein the at least one first rule includes at least one similarity rule and the at least one second rule includes at least one clustering rule.

3. The method of claim 2, wherein the at least one similarity rule includes comparing patient data attributes included in the medical information.

4. The method of claim 3 further comprising computing a distance between the patient data attributes and the clustered medical information.

5. The method of claim 4, wherein if the distance is less than a threshold, then the clustered medical information is included as an additional referral that does not appear in the reported-referral data.

6. The method of claim 1, wherein the metrics are generated for in network referrals and out of network referrals.

7. A medical information navigation engine ("MINE") comprising:

an interface server configured to:
    receive, via at least one secure communication link, medical information from a plurality of medical data sources, the medical information including visit-note data and reported-referral data, the medical information received in different formats; and
    transmit the medical information to a database in encrypted form, the medical information reformatted into a single format by a back-end server, the database configured to store the reformatted and encrypted medical information;

the back-end server configured to:
    reformat the medical information by converting the different formats into the single format that facilitates reconciling and de-duplicating of the medical information;
    retrieve, from the database, the reformatted and encrypted medical information;
    build an intent-based clustering model by applying a set of rules to the retrieved medical information, wherein the intent-based clustering model is configured to identify one or more referrals within the retrieved medical information and other retrieved medical information, and wherein applying the set of rules comprises:
    (i) identifying one or more similarities within the retrieved medical information and defining characteristics of the retrieved medical information by applying at least one first rule of the set of rules to the retrieved medical information, wherein the at least one first rule is configured to learn to detect similarities using first feedback data associated with a plurality of medical information received by the MINE,
    ii) clustering the retrieved medical information into one or more groups by applying at least one second rule of the set of rules to the identified one or more similarities, wherein the at least one second rule is configured to learn to detect clusters using second feedback data associated with the plurality of medical information received by the MINE, and
    (iii) identifying information within the retrieved medical information that has changed over time by applying at least one third rule of the set of rules to the one or more groups, wherein the at least one third rule is configured to learn to detect changes over time using third feedback data associated with the plurality of medical information received by the MINE; and
    infer, by based on the application of the intent-based clustering model to the retrieved medical information, unreported referrals, the unreported referrals comprising instances in which a referral of the one or more referrals detected by the intent-based clustering model does not appear in the reported-referral data; and a front-end server configured to:

generate metrics by (i) adding reported referral activity in the reported-referral data to the inferred unreported referrals to generate a combined referral number and (ii) dividing the reported referral activity by the combined referral number; and display an analytical dashboard on a user interface of a user computing device, the analytical dashboard displaying the generated metrics including one or more charts.

8. The MINE of claim 7, wherein the back-end server further comprises:

a reconciliation engine configured to apply the at least one first rule to the retrieved medical information; and an intent-based presentation engine configured to apply the at least one second rule to the identified one or more similarities.

9. The MINE of claim 7, wherein the at least one first rule includes at least one similarity rule and the at least one second rule includes at least one clustering rule.

10. The MINE of claim 9 wherein the at least one similarity rule includes comparing patient data attributes included in the medical information.

11. The MINE of claim 10, wherein the back-end server is further configured to compute a distance between the patient data attributes and the clustered medical information.

12. The MINE of claim 11, wherein if the distance is less than a threshold, then the clustered medical information is included as an additional referral that does not appear in the reported-referral data.

13. The MINE of claim 7, wherein the front-end server is further configured to generate the metrics for in network referrals and out of network referrals.

14. The method of claim 1 further comprising:

receiving, by the back-end server, a user query for the medical information requested by a user;

querying, by the front-end server, the database by converting the user query into one or more commands compliant with a medical search engine configured to return results for the user query; and displaying, by the front-end server via an Application Programming Interface (API) call, the results on the user interface of the user computing device.

15. The MINE of claim 7 further, wherein the back-end server is further configured to receive a user query for the medical information requested by a user, and wherein the front-end server is further configured to:

query the database by converting the user query into one or more commands compliant with a medical search engine configured to return results for the user query; and display, via an Application Programming Interface (API) call, the results on the user interface of the user computing device.

* * * * *